United States Patent
Xu et al.

(10) Patent No.: US 10,238,623 B2
(45) Date of Patent: Mar. 26, 2019

(54) C14-HYDROXYL ESTERIFIED AMINO ACID DERIVATIVE OF TRIPTOLIDE, AND PREPARATION METHOD AND USE THEREOF

(71) Applicant: HANGZHOU WEBEN PHARMACEUTICALS INC, Hangzhou, Zhejiang (CN)

(72) Inventors: Rongzhen Xu, Hangzhou (CN); Hongjian Jiang, Hangzhou (CN)

(73) Assignee: HANGZHOU WEBEN PHARMACEUTICALS INC, Hangzhou, Zhejiang (CN)

(*) Notice: Subject to any disclaimer, the term of this patent is extended or adjusted under 35 U.S.C. 154(b) by 0 days.

(21) Appl. No.: 15/551,695

(22) PCT Filed: Oct. 29, 2015

(86) PCT No.: PCT/CN2015/093161
§ 371 (c)(1),
(2) Date: Aug. 17, 2017

(87) PCT Pub. No.: WO2017/070878
PCT Pub. Date: May 4, 2017

(65) Prior Publication Data
US 2018/0036277 A1 Feb. 8, 2018

(51) Int. Cl.
| | |
|---|---|
| C07D 307/77 | (2006.01) |
| A61K 31/343 | (2006.01) |
| A61K 31/365 | (2006.01) |
| A61K 31/585 | (2006.01) |
| C07D 493/22 | (2006.01) |
| C07D 303/06 | (2006.01) |
| A61P 35/00 | (2006.01) |
| A61P 37/00 | (2006.01) |

(52) U.S. Cl.
CPC .......... *A61K 31/343* (2013.01); *A61K 31/365* (2013.01); *A61K 31/585* (2013.01); *A61P 35/00* (2018.01); *A61P 37/00* (2018.01); *C07D 303/06* (2013.01); *C07D 307/77* (2013.01); *C07D 493/22* (2013.01)

(58) Field of Classification Search
CPC .................................................. C07D 307/77
See application file for complete search history.

(56) References Cited

FOREIGN PATENT DOCUMENTS

| CN | 1246121 A | 3/2000 |
| CN | 103816548 * | 5/2014 |
| WO | 1998/52951 A1 | 11/1998 |
| WO | 02074759 A1 | 9/2002 |
| WO | 2008087202 A1 | 7/2008 |

OTHER PUBLICATIONS

Xu et al., Design, synthesis, and biological evaluation of novel water-soluble triptolide derivatives: Antineoplastic activity against imatinib-resistant CML cells bearing T315I mutant Bcr-Abl. Bioorg Med Chem. Mar. 1, 2010;18 (5):1806-15.

Zhuang et al., Simultaneous determination of triptolide and its prodrug MC002 in dog blood by LC-MS/MS and its application in pharmacokinetic studies. J Ethnopharmacol. Oct. 28, 2013;150(1):131-7.

Supplementary European Search Report for Application No. 15906944.2, dated Jun. 19, 2018. 11 pages.

* cited by examiner

*Primary Examiner* — Brian E McDowell
(74) *Attorney, Agent, or Firm* — McCarter & English, LLP; Steven G. Davis; Wei Song

(57) ABSTRACT

The present invention belongs to the field of natural medicines and medicinal chemistry, and relates to novel esterified amino acid derivatives of triptolide of general formula I and general formula II or pharmaceutically acceptable adducts, complexes, salts, and catabolites and metabolites thereof, preparation methods of these compounds, pharmaceutical compositions comprising the compound, and uses thereof in preparing drugs against tumors, immune diseases, or diseases related to abnormal expression of XPB or Pol II or oncogene c-myc.

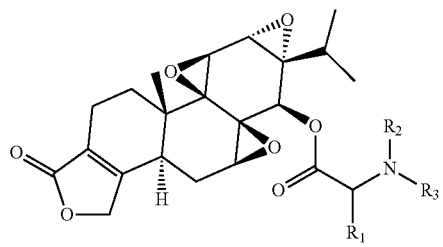

3 Claims, 1 Drawing Sheet

C14-HYDROXYL ESTERIFIED AMINO ACID DERIVATIVE OF TRIPTOLIDE, AND PREPARATION METHOD AND USE THEREOF

CROSS-REFERENCE TO RELATED APPLICATIONS

This application is a U.S. national stage filing, under 35 U.S.C § 371 (c), of International Application No. PCT/CN2015/093161, filed on Oct. 29, 2015. The entire contents of the aforementioned application are incorporated herein by reference.

TECHNICAL FIELD

The present invention belongs to the field of natural medicines and medicinal chemistry, and more particularly to novel triptolide derivatives, especially C14-hydroxyl esterified amino acid derivatives of triptolide, and preparation methods and uses of these compounds.

BACKGROUND OF THE INVENTION

Triptolide (TPL) is an abietane diterpene lactone compound with a unique configuration containing 3 epoxy groups and an α, β-unsaturated five-membered lactone ring structure, which is isolated from *Tripterygium wilfordii* Hook. f., a plant of the genus *Tripterygium* of the family Celastraceae. It has a molecular formula of $C_{20}H_{24}O_6$, a molecular weight of 360.4, and a structural formula shown below.

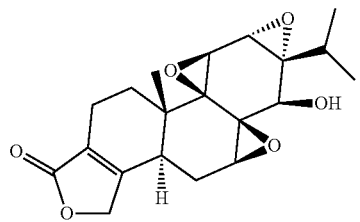 [SMILES: CC(C)[C@]12O[C@H]1[C@@H]1O[C@]13[C@]1(O[C@H]1C[C@H]1C4=C(CC[C@@]13C)C(=O)OC4)[C@@H]2O]

A large number of in vivo and in vitro studies have shown that triptolide has significant biological activities such as anti-tumor activity, anti-inflammatory activity, immunosuppressive activity, and anti-male fertility activity. Triptolide can significantly prolong the survival time of L615 leukemia mice, and also shows a significant therapeutic effect for human leukemia with a complete remission rate of up to 40% (18/45) [Xia Zhi-Lin et al., "Pharmacological and Clinical Studies of Triptolide." Acta Pharmacologica Sinica, 1992, (6)427-431]. It is clinically used for the treatment of psoriasis, rheumatoid arthritis, leukemia, nephropathy, etc. Studies on the toxicity of triptolide, however, demonstrate that triptolide has high toxicity and a narrow therapeutic window, and has serious toxic side effects on the digestive system, urogenital system and hematological system, etc. Therefore, the clinical development research of triptolide is limited to some extent. Due to its unique chemical structure and biological activities, triptolide has received great interest from chemists and pharmacologists in various countries. In order to reveal the mechanism of action and structure-activity relationship of triptolide and to find its derivatives with high activity and low toxicity, several study groups have made systematic studies on triptolide and its analogues and have synthesized a series of triptolide derivatives [Zhang Fan et al., "Progress in Structure Modification of Triptolide." Acta Pharmacologica Sinica, 2004, 39(10):857-864; and Tai Ting et al., "Advance in Pharmacokinetics of Triptolide." Pharmaceutical and Clinical Research, 2012, 20(3):229-235]. Some of them have entered clinical trials. For example, Minnelide, a water-soluble prodrug of triptolide synthesized by scientists of the University of Minnesota, USA, can convert into triptolide both in vivo and in vitro. In some animal models, Minnelide showed good anti-cancer effect and less toxic reaction. For example, in a nude mouse model of pancreatic cancer, Minnelide prolonged the survival of mice by reducing the tumor volume and the spread of the tumor, and Minnelide showed no significant toxic effect at a dosage effective to tumor regression. Minnelide is now entering phase I clinical trials [Chugh R, et al., "A preclinical evaluation of Minnelide as a therapeutic agent against pancreatic cancer." Sci Transl Med., 2012; 4(156):156ra139.]. Unfortunately, no triptolide or derivatives thereof has been found to enter phase II clinical trials so far. Therefore, researchers still need to make further studies in order to explore methods related to safe clinical application of triptolide as well as novel triptolide derivatives with high activity and low toxicity. In addition, the pharmacokinetic characteristics of triptolide for both oral and intravenous injection suggest that triptolide has a short elimination half-life, undergoes fast absorption, distribution, metabolism, and elimination in body, and the plasma drug concentration and tissue drug concentrations of which fluctuate greatly over time. Hence, triptolide does not have ideal pharmacokinetic properties, and are unfavorable for clinical application, and might increase the incidence of clinical adverse reactions. Thus, it is very significant to explore novel triptolide derivatives and relevant formulations with good pharmacokinetic characteristics [Tai Ting et al., "Advance in Pharmacokinetics of Triptolide." Pharmaceutical and Clinical Research, 2012, 20(3):229-235].

Therefore, there is still a need in the market for triptolide drugs with good biological activities and pharmacokinetic characteristics and less toxicity. So far, there are still no reports on the synthesis and application of triptolide derivatives with these characteristics.

SUMMARY OF THE INVENTION

The first object of the present invention is to provide a novel C14-hydroxyl esterified amino acid derivative of triptolide of general formula (I) characterized by single amino acid esterification, or a pharmaceutically acceptable adduct, complex, salt, catabolite, and metabolite thereof, and to provide a novel C14-hydroxyl esterified amino acid derivative of triptolide of general formula (II) characterized by dipeptide esterification, or a pharmaceutically acceptable adduct, complex, salt, catabolite, and metabolite thereof:

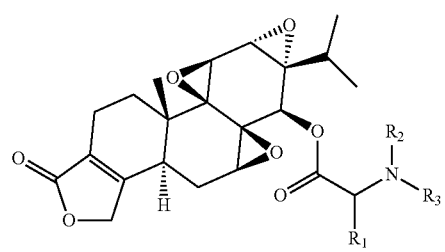

I

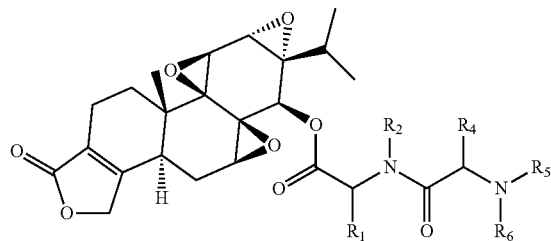

wherein $R_1$ is selected from substituted or unsubstituted $C_2$-$C_{20}$ alkyl, substituted or unsubstituted $C_2$-$C_{20}$ alkenyl, substituted or unsubstituted $C_4$-$C_{20}$ conjugated alkenyl, substituted or unsubstituted $C_3$-$C_7$ cycloalkyl or cycloalkenyl, substituted or unsubstituted aryl, substituted or unsubstituted heterocyclyl and aromatic heterocyclyl, and substituted or unsubstituted amino acid side-chain alkyl; the amino acid may be racemic, or may be optically pure (levorotary or dextrorotary); the substituents are selected from halogen, amino, $C_1$-$C_6$ substituted amino, nitro, cyano, hydroxyl, $C_1$-$C_6$ alkoxy, mercapto, and $C_1$-$C_6$ alkylthio;

wherein $R_2$ and $R_3$ are selected from H, substituted or unsubstituted $C_1$-$C_{20}$ alkyl, substituted or unsubstituted $C_2$-$C_{20}$ alkenyl, substituted or unsubstituted $C_4$-$C_{20}$ conjugated alkenyl, substituted or unsubstituted $C_3$-$C_7$ cycloalkyl or cycloalkenyl, substituted or unsubstituted aryl, substituted or unsubstituted heterocyclyl and aromatic heterocyclyl, and substituted or unsubstituted amino acid side-chain alkyl, the amino acid may be racemic, or may be optically pure (levorotary or dextrorotary); the substituents are selected from halogen, amino, $C_1$-$C_6$ substituted amino, nitro, cyano, hydroxyl, $C_1$-$C_6$ alkoxy, mercapto, and $C_1$-$C_6$ alkylthio; $R_2$ and $R_3$ may be protecting groups that are Boc, Fmoc, Bn, Cbz, or the like; $R_2$ and $R_3$ may be the same or different;

wherein $R_4$ is selected from substituted or unsubstituted $C_2$-$C_{20}$ alkyl, substituted or unsubstituted $C_2$-$C_{20}$ alkenyl, substituted or unsubstituted $C_4$-$C_{20}$ conjugated alkenyl, substituted or unsubstituted $C_3$-$C_7$ cycloalkyl or cycloalkenyl, substituted or unsubstituted aryl, substituted or unsubstituted heterocyclyl and aromatic heterocyclyl, and substituted or unsubstituted amino acid side-chain alkyl, the amino acid may be racemic, or may be optically pure (levorotary or dextrorotary); the substituents are selected from halogen, amino, $C_1$-$C_6$ substituted amino, nitro, cyano, hydroxyl, $C_1$-$C_6$ alkoxy, mercapto, and $C_1$-$C_6$ alkylthio;

wherein $R_5$ and $R_6$ are selected from H, substituted or unsubstituted $C_1$-$C_{20}$ alkyl, substituted or unsubstituted $C_2$-$C_{20}$ alkenyl, substituted or unsubstituted $C_4$-$C_{20}$ conjugated alkenyl, substituted or unsubstituted $C_3$-$C_7$ cycloalkyl or cycloalkenyl, substituted or unsubstituted aryl, substituted or unsubstituted heterocyclyl and aromatic heterocyclyl, and substituted or unsubstituted amino acid side-chain alkyl, the amino acid may be racemic, or may be optically pure, including levorotary and dextrorotary; the substituents are selected from halogen, amino, $C_1$-$C_6$ substituted amino, nitro, cyano, hydroxyl, $C_1$-$C_6$ alkoxy, mercapto, and $C_1$-$C_6$ alkylthio; $R_5$ and $R_6$ may be protecting groups that are Boc, Fmoc, Bn, Cbz, or the like; $R_5$ and $R_6$ may be the same or different.

The second object of the present invention is to provide methods of preparing the C14-hydroxyl esterified amino acid derivatives of triptolide with single amino acid esterification of general formula (I) and with dipeptide esterification of general formula (II) of the present invention, which are carried out according to the following schemes:

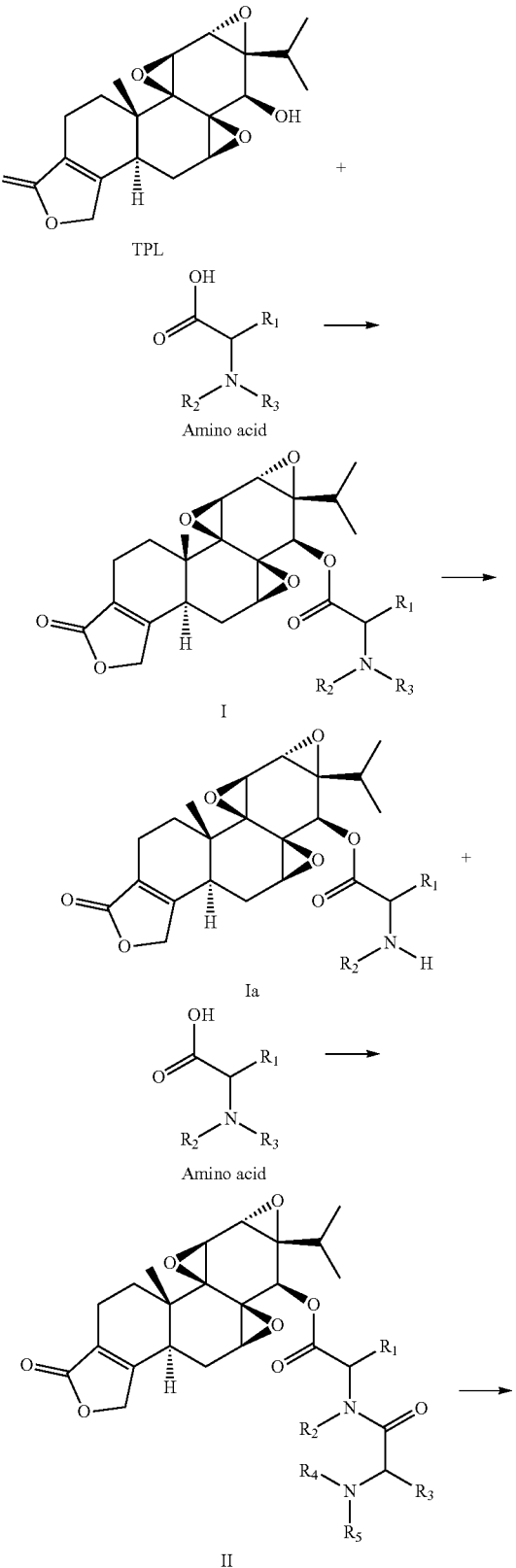

-continued

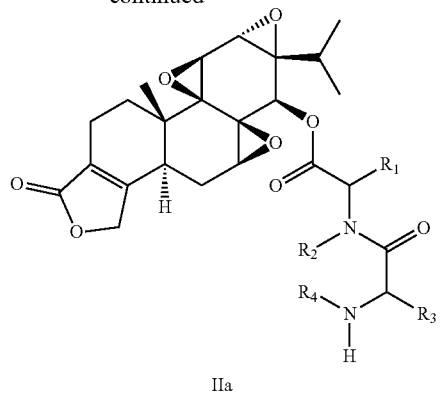

IIa

The C14-hydroxyl esterified amino acid derivative of triptolide with single amino acid esterification of general formula (I) may be formed through the esterification condensation of triptolide with respective amino acids $R_2R_3NCHR_1CO_2H$ in the presence of a condensing agent or catalyst in a suitable solvent at an appropriate temperature; and may also be formed through the esterification condensation of triptolide with respective amino acid acyl chlorides $R_2R_3NCHR_1COCl$ in the presence of a basic agent; or through the activation of amino acid $R_2R_3NCHR_1CO_2H$ to generate an active ester intermediate, which then reacted with triptolide to generate the C14-hydroxyl esterified amino acid derivative of triptolide (I); and may also through the activation of amino acid $R_2R_3NCHR_1CO_2H$ to generate a mixed anhydride intermediate, which then reacted with triptolide to generate the C14-hydroxyl esterified amino acid derivative of triptolide (I). $R_1$, $R_2$, $R_3$ in the formula (I), $R_1$, $R_2$, $R_3$ in the amino acid $R_2R_3NCHR_1CO_2H$, $R_1$, $R_2$, $R_3$ in the amino acid acyl chloride $R_2R_3NCHR_1COCl$, $R_1$, $R_2$, $R_3$ in the active ester intermediate, and $R_1$, $R_2$, $R_3$ in the mixed anhydride intermediate all have the same definitions as those in the formula (I) above.

The present invention also provides a method of preparing the C14-hydroxyl esterified amino acid derivative of triptolide with dipeptide esterification of general formula (II) of the present invention: The C14-hydroxyl esterified amino acid derivative of triptolide with dipeptide esterification (II) may be prepared by first preparing the C14-hydroxyl esterified amino acid derivative of triptolide (I) according to the foregoing method, wherein in the amino acid $R_2R_3NCHR_1CO_2H$ used, $R_2$ or $R_3$ is a protecting group. The amino-protecting groups are known to those skilled in the art, and can be easily found in literature resources, for example, Greene and Wuts, "Protective Groups in Organic Synthesis," 3rd edition, John Wiley & Sons Press, New York, N.Y., 1999, the entirety of which is incorporated herein by reference. Then, the protecting group is removed to obtain a derivative of general formula Ia, which is further subjected to amidation condensation with respective amino acids $R_5R_6NCHR_4CO_2H$ in the presence of a condensing agent or catalyst in a suitable solvent at an appropriate temperature, to generate the C14-hydroxyl esterified amino acid derivative of triptolide with dipeptide esterification (II); and the derivative of general formula Ia obtained by the removal of the protecting group may also be subjected to amidation condensation with respective amino acid acyl chlorides $R_5R_6NCHR_4COCl$ in the presence of a basic agent, to generate the C14-hydroxyl esterified amino acid derivative of triptolide with dipeptide esterification (II); or the C14-hydroxyl esterified amino acid derivative of triptolide with dipeptide esterification (II) may be generated through the activation of amino acid $R_5R_6NCHR_4CO_2H$ to generate an active ester intermediate, which then reacted with the C14-hydroxyl esterified amino acid derivative of triptolide (Ia); and may also be generated through the activation of amino acid $R_5R_6NCHR_4CO_2H$ to generate a mixed anhydride intermediate, which then reacted with the C14-hydroxyl esterified amino acid derivative of triptolide (Ia). When $R_5$ or $R_6$ is a protecting group, a compound IIa may be obtained by further removing the protecting group. $R_1$, $R_2$, $R_3$, $R_4$, $R_5$ and $R_6$ in the formula (II), $R_1$, $R_2$, $R_3$ in the amino acid $R_2R_3NCHR_1CO_4H$, $R_1$, $R_2$, $R_3$ in the amino acid acyl chloride $R_2R_5NCHR_6COCl$, $R_1$, $R_2$, $R_3$ in the active ester intermediate, and $R_1$, $R_2$, $R_3$ in the mixed anhydride intermediate all have the same definitions as those in the formula (II) above. $R_4$, $R_5$, $R_6$ in the amino acid $R_5R_6NCHR_4CO_2H$, $R_4$, $R_5$, $R_6$ in the amino acid acyl chloride $R_5R_6NCHR_4COCl$, $R_4$, $R_5$, $R_6$ in the active ester intermediate, and $R_4$, $R_5$, $R_6$ in the mixed anhydride intermediate all have the same definitions as those in the formula (II) above.

The third object of the present invention is to provide a pharmaceutical composition, comprising at least one compound of the present invention and an optional pharmaceutically acceptable excipient, wherein the compound is selected from the C14-hydroxyl esterified amino acid derivative of triptolide with single amino acid esterification of general formula (I) and the C14-hydroxyl esterified amino acid derivative of triptolide with dipeptide esterification of general formula (II).

The fourth object of the present invention is to provide a use of the compound or the pharmaceutical composition comprising the compound of the present invention in preparing a drug, particularly an anti-tumor drug. Accordingly, the present invention provides a method of treating a patient having a tumor, comprising administering to the patient in need of such treatment a therapeutically effective amount of at least one compound of the present invention. In particular, the tumor is selected from leukemia, multiple myeloma, lymphoma, liver cancer, stomach cancer, breast cancer, cholangiocarcinoma, pancreatic cancer, lung cancer, colorectal cancer, osteosarcoma, melanoma, human cervical cancer, glioma, nasopharyngeal carcinoma, laryngeal cancer, esophageal cancer, middle ear tumor, prostate cancer, and the like. The compound is selected from the C14-hydroxyl esterified amino acid derivative of triptolide with single amino acid esterification of general formula (I) and the C14-hydroxyl esterified amino acid derivative of triptolide with dipeptide esterification of general formula (II).

The fifth object of the present invention is to provide a use of the compound or the pharmaceutical composition comprising the compound of the present invention in preparing a drug for treating an autoimmune disease. In particular, the autoimmune disease is selected from autoimmune diseases related to dysfunction of immune cells such as T cells or B cells, and the autoimmune disease is, for example, rheumatoid arthritis, systemic lupus erythematosus, psoriasis, nephropathy, and the like. The compound is selected from the C14-hydroxyl esterified amino acid derivative of triptolide with single amino acid esterification of general formula (I) and the C14-hydroxyl esterified amino acid derivative of triptolide with dipeptide esterification of general formula (II).

DETAILED DESCRIPTION OF THE INVENTION

The present invention relates to novel C14-hydroxyl esterified amino acid derivatives of triptolide with single amino acid esterification of general formula (I) and with dipeptide esterification of general formula (II), or pharmaceutically acceptable adducts, complexes, salts, catabolites and metabolites thereof:

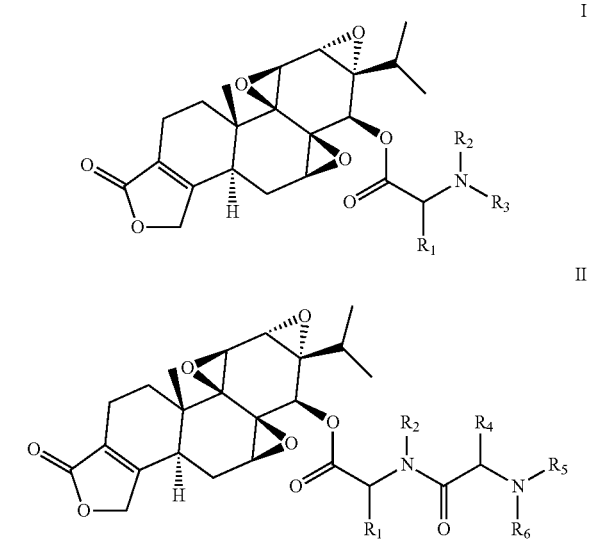

wherein $R_1$ is selected from substituted or unsubstituted $C_2$-$C_{20}$ alkyl, substituted or unsubstituted $C_2$-$C_{20}$ alkenyl, substituted or unsubstituted $C_4$-$C_{20}$ conjugated alkenyl, substituted or unsubstituted $C_3$-$C_7$ cycloalkyl or cycloalkenyl, substituted or unsubstituted aryl, substituted or unsubstituted heterocyclyl and aromatic heterocyclyl, and substituted or unsubstituted amino acid side-chain alkyl, the amino acid may be racemic, or may be optically pure (levorotary or dextrorotary); the substituents are selected from halogen, amino, $C_1$-$C_6$ substituted amino, nitro, cyano, hydroxyl, $C_1$-$C_6$ alkoxy, mercapto, and $C_1$-$C_6$ alkylthio;

wherein $R_2$, $R_3$, $R_4$, $R_5$ and $R_6$ are selected from H, substituted or unsubstituted $C_1$-$C_{20}$ alkyl, substituted or unsubstituted $C_2$-$C_{20}$ alkenyl, substituted or unsubstituted $C_4$-$C_{20}$ conjugated alkenyl, substituted or unsubstituted $C_3$-$C_7$ cycloalkyl or cycloalkenyl, substituted or unsubstituted aryl, substituted or unsubstituted heterocyclyl and aromatic heterocyclyl, and substituted or unsubstituted amino acid side-chain alkyl, the amino acid may be racemic, or may be optically pure (levorotary or dextrorotary); the substituents are selected from halogen, amino, $C_1$-$C_6$ substituted amino, nitro, cyano, hydroxyl, $C_1$-$C_6$ alkoxy, mercapto, and $C_1$-$C_6$ alkylthio; $R_2$ and $R_3$, $R_5$ and $R_6$ may be protecting groups that are Boc, Fmoc, Bn, Cbz, or the like; $R_2$ and $R_3$ may be the same or different; $R_5$ and $R_6$ may be the same or different.

In one embodiment, the present invention relates to a compound of general formula I or general formula II, wherein $R_1$ and $R_4$ are selected from substituted or unsubstituted $C_2$-$C_{20}$ alkyl. $R_1$ and $R_4$ may be the same or different.

In one embodiment, the present invention relates to a compound of general formula I or general formula II, wherein $R_2$, $R_3$, $R_5$ and $R_6$ are selected from H and substituted or unsubstituted $C_1$-$C_{20}$ alkyl. $R_2$, $R_3$, $R_5$ and $R_6$ may be the same or different.

In one embodiment, the present invention relates to a compound of general formula I or general formula II, wherein $R_1$, $R_2$, $R_3$, $R_4$, $R_5$ and $R_6$ are selected from substituted or unsubstituted $C_2$-$C_{20}$ alkenyl and substituted or unsubstituted $C_4$-$C_{20}$ conjugated alkenyl. $R_1$, $R_2$, $R_3$, $R_4$, $R_5$ and $R_6$ may be the same or different.

In one embodiment, the present invention relates to a compound of general formula I or general formula II, wherein $R_1$, $R_2$, $R_3$, $R_4$, $R_5$ and $R_6$ are selected from substituted or unsubstituted $C_3$-$C_7$ cycloalkyl or cycloalkenyl. $R_1$, $R_2$, $R_3$, $R_4$, $R_5$ and $R_6$ may be the same or different.

In one embodiment, the present invention relates to a compound of general formula I or general formula II, wherein $R_1$, $R_2$, $R_3$, $R_4$, $R_5$ and $R_6$ are selected from substituted or unsubstituted aryl. $R_1$, $R_2$, $R_3$, $R_4$, $R_5$ and $R_6$ may be the same or different.

In one embodiment, the present invention relates to a compound of general formula I or general formula II, wherein $R_1$, $R_2$, $R_3$, $R_4$, $R_5$ and $R_6$ are selected from substituted or unsubstituted heterocyclyl or aromatic heterocyclyl. $R_1$, $R_2$, $R_3$, $R_4$, $R_5$ and $R_6$ may be the same or different.

In one embodiment, the present invention relates to a compound of general formula I or general formula II, wherein $R_1$, $R_2$, $R_3$, $R_4$, $R_5$ and $R_6$ are selected from substituted or unsubstituted amino acid side-chain alkyl. $R_1$, $R_2$, $R_3$, $R_4$, $R_5$ and $R_6$ may be the same or different.

Some amino acid derivatives of triptolide of the present invention are shown below. These examples merely give a further illustration of the present invention, and are not intended to limit the scope of the present invention in any way.

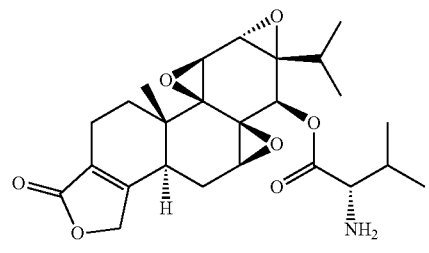

14-L-Valine-TPL

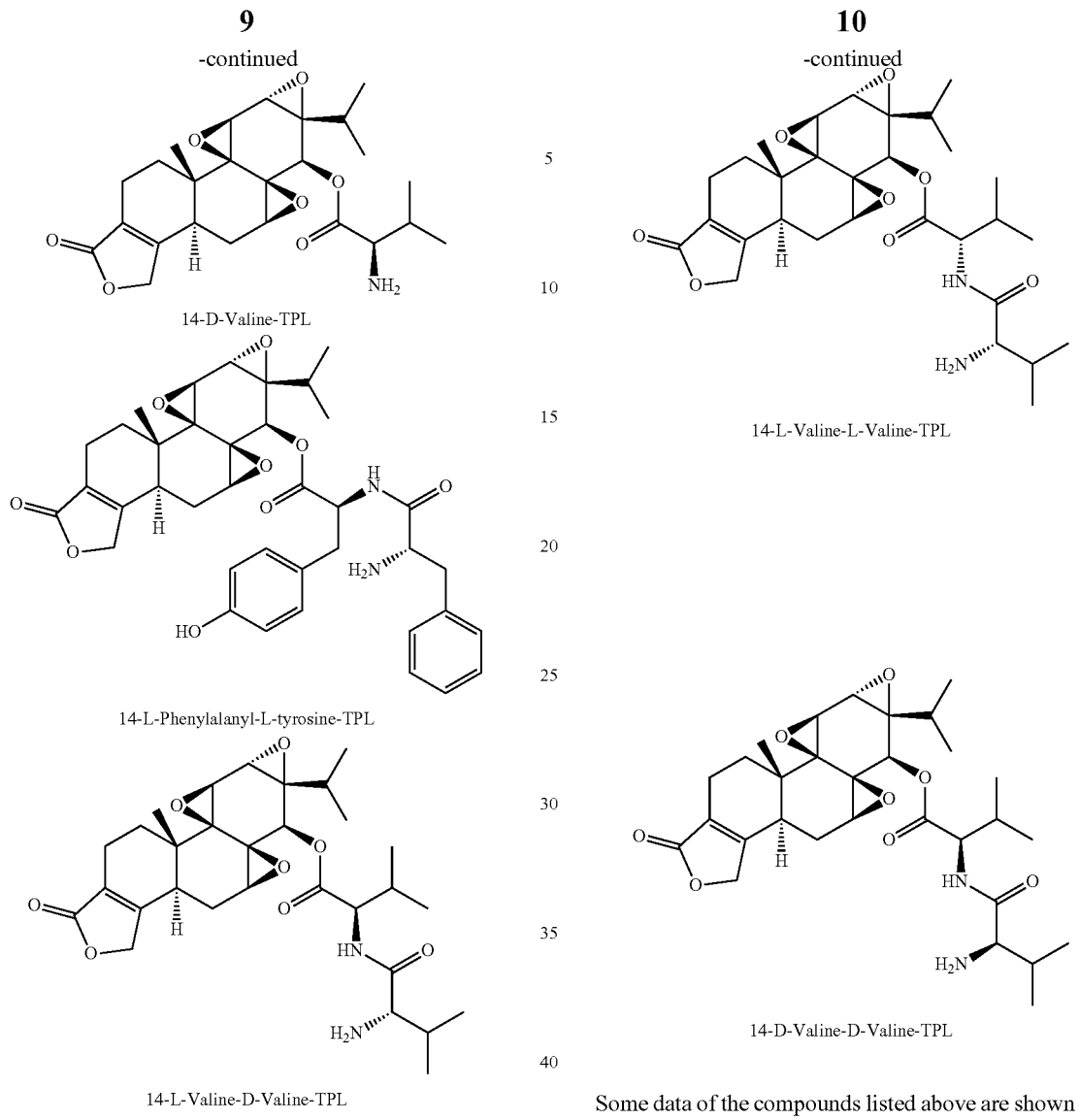

Some data of the compounds listed above are shown in the table below.

| No. | Name | Molecular Formula | Molecular Weight | Appearance | State |
|---|---|---|---|---|---|
| 001 | 14-D-Valine-TPL (14-Dextro-Valine-Triptolide) | $C_{25}H_{33}NO_7$ | 459.3 | white | powdery solid |
| 002 | 14-L-Valine-TPL (14-Levo-Valine-Triptolide) | $C_{25}H_{33}NO_7$ | 459.3 | white | powdery solid |
| 003 | 14-D-Valine-D-Valine-TPL (14-Dextro-Valine-Dextro-Triptolide) | $C_{30}H_{42}N_2O_8$ | 558.66 | white | powdery solid |
| 004 | 14-L-Valine-L-Valine-TPL (14-Levo-Valine-Levo-Triptolide) | $C_{30}H_{42}N_2O_8$ | 558.66 | white | powdery solid |
| 005 | 14-L-Phenylalanyl-L-tyrosine-TPL (14-Levo-Phenylalanyl-Levo-tyrosine-Triptolide) | $C_{38}H_{42}N_2O_9$ | 670.75 | white | powdery solid |
| 006 | 14-L-Valine-D-Valine-TPL (14-Levo-Valine-Dextro-Valine-Triptolide) | $C_{30}H_{42}N_2O_8$ | 558.66 | white | powdery solid |

In another embodiment, the following compounds of general formula (I) are particularly preferred in the present invention:

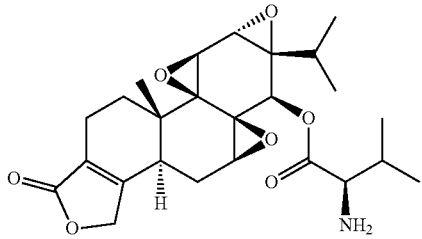

14-D-Valine-TPL
14-D-Valine-TPL (14-Dextro-Valine-Tripolide)

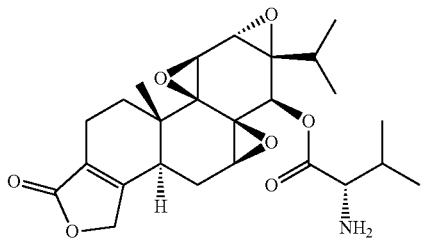

14-L-Valine-TPL
14-L-Valine-TPL (14-Levo-Valine-Tripolide)

In another embodiment, the following compounds of general formula (II) are particularly preferred in the present invention:

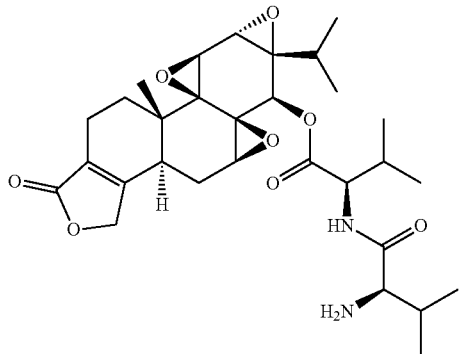

14-D-Valine-D-Valine-TPL
14-D-Valine-D-Valine-TPL (14-Dextro-Valine-Dextro-Valine-Triptolide)

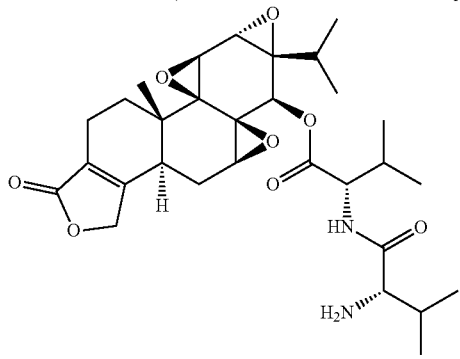

14-L-Valine-L-Valine-TPL
14-L-Valine-L-Valine-TPL (14-Levo-Valine-Levo-Valine-Triptolide)

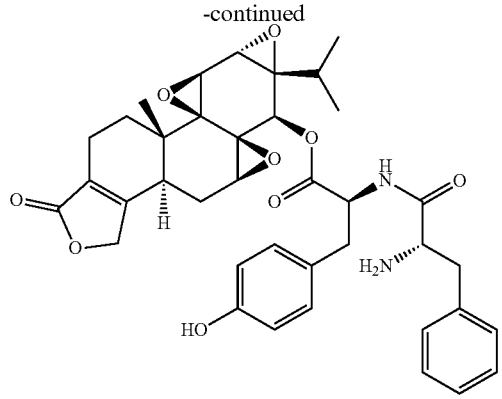

14-L-Phenylalanyl-L-tyrosine-TPL
14-L-Phenylalanyl-L-tyrosine-TPL (14-Levo-Phenylalanyl-Levo-tyrosine-Triptolide)

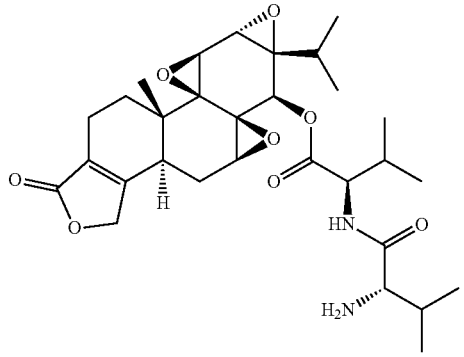

14-L-Valine-D-Valine-TPL
14-L-Valine-D-Valine-TPL (14-Levo-Dextro-Valine-Triptolide)

The present invention relates to compounds of general formula (I) and general formula (II) of the present invention in the form of: salts, solvates, hydrates, adducts, complexes, polymorphs or prodrugs thereof.

As used herein, the term "$C_1$-$C_{20}$ alkyl" refers to a linear or branched, substituted or unsubstituted alkyl containing 1-20 carbon atoms. Examples of $C_1$-$C_{20}$ alkyl include, but are not limited to, methyl, ethyl, n-propyl, isopropyl, n-butyl, isobutyl, t-butyl, n-pentyl, n-hexyl, and n-eicosyl.

The term "$C_2$-$C_{20}$ alkyl" refers to a linear or branched, substituted or unsubstituted alkyl containing 2-20 carbon atoms. Examples of $C_2$-$C_{20}$ alkyl include, but are not limited to, ethyl, n-propyl, isopropyl, n-butyl, isobutyl, t-butyl, n-pentyl, n-hexyl, and n-eicosyl.

The term "$C_2$-$C_{20}$ alkenyl" refers to a linear or branched, substituted or unsubstituted alkenyl containing 2-20 carbon atoms. Examples of $C_2$-$C_{20}$ alkenyl include, but are not limited to, vinyl, allyl, and eicosenyl.

The term "$C_4$-$C_{20}$ conjugated alkenyl" refers to a linear or branched, substituted or unsubstituted conjugated alkenyl containing 4-20 carbon atoms. Examples of $C_4$-$C_{20}$ conjugated alkenyl include, but are not limited to, conjugated butadiene group, retinoyl, and (9Z)-octadecanoyl-9-alkenyl.

The term "$C_3$-$C_7$ cycloalkyl or cycloalkenyl" refers to a hydrocarbon group of 3-7 membered monocyclic system with a saturated or unsaturated ring, and $C_3$-$C_7$ cycloalkyl may be cyclopropyl, cyclobutyl, cyclopentyl, cyclohexyl, cycloheptyl, cyclopropenyl, and cyclohexenyl.

The term "aryl" refers to an aryl containing no heteroatoms, including aryl, aryl alkyl, and alkyl aryl.

The term "heterocyclic aryl" refers to an aryl containing heteroatoms, including heterocyclic aryl, heterocyclic aryl alkyl, and alkyl heterocyclic aryl. Heteroatoms refer to nitrogen, oxygen, and sulfur. Heterocyclic aryl may contain one heteroatom or contain several heteroatoms at the same time.

The term "amino acid" refers to a natural amino acid or a non-natural amino acid.

The term "halogen" refers to fluorine, chlorine, bromine, or iodine.

The term "$C_1$-$C_6$ substituted amino" refers to —N—$C_1$-$C_6$ alkyl and —N—$C_3$-$C_6$ cycloalkyl.

The term "$C_1$-$C_6$ alkoxy" refers to —O—$C_1$-$C_6$ alkyl and —O—$C_3$-$C_6$ cycloalkyl.

The term "$C_1$-$C_6$ alkylthio" refers to —S—$C_1$-$C_6$ alkyl and —S—$C_3$-$C_6$ cycloalkyl.

The term "pharmaceutically acceptable adducts and complexes of the compounds of formula (I) and formula (II)" refer to the products formed when the compounds of the present invention further bind to other small molecules or bio-macromolecules with non-chemical bonds or non-covalent intermolecular forces.

As used herein, the term "pharmaceutically acceptable salts of the compounds of general formula (I) and general formula (II)" refer to organic acid salts formed by the compounds of the present invention and organic acids having pharmaceutically acceptable anions. The organic acid salt includes, but are not limited to, tosylate, mesylate, malate, acetate, citrate, malonate, tartrate, succinate, benzoate, ascorbate, lactate, α-ketoglutarate, and α-glycerophosphate; suitable inorganic salts may also be formed, including, but not limited to, hydrochloride, sulfate, nitrate, bicarbonate and carbonate, phosphate, hydrobromide, hydroiodide, and the like.

Pharmaceutically acceptable salts may be obtained using standard procedures well known in the art, for example, through the reaction of a sufficient amount of a basic compound and a suitable acid providing a pharmaceutically acceptable anion.

As used herein, the term "polymorph" refers to the solid crystal form of the compounds of the present invention or complexes thereof. Different polymorphs of the same compound may exhibit different physical, chemical and/or spectral properties. Different physical properties include, but are not limited to, stability (for example, to heat or light), compressibility and density (important to formulation preparation and product manufacturing), and dissolution rate (which may affect bioabsorbability and bioavailability). Differences in stability will lead to the changes in chemical reactivity (for example, differential oxidation, such that a dosage form discolors more rapidly when comprised of one polymorph than when comprised of another polymorph), or mechanical performance (e.g., tablet crumble of a polymorph as being kinetically favored while in storage converts to a more thermodynamically stable polymorph), or both (e.g., tablets of one polymorph are more susceptible to breakdown at high humidity). Different physical properties of polymorphs may affect their processing. For example, one polymorph may be more likely to form a solvate or may be more difficult to filter or wash free of impurities than another, and this is because of, for example, the shape or size distribution of their particles.

As used herein, the term "hydrate" refers to the compound of the present invention or the salt thereof which further comprises a stoichiometric or non-stoichiometric amount of water bound by non-covalent intermolecular forces.

As used herein, the term "prodrug" refers to a derivative that can undergo hydrolyzation, oxidization or other reactions under biological conditions (in vitro or in vivo) to provide the compound of the present invention, unless otherwise indicated. Prodrugs may only become active compounds after undergoing such reaction under biological conditions, or they may be active in their unreacted forms. Prodrugs may typically be prepared using well-known methods, for example, those described in 1 Burger's Medicinal Chemistry and Drug Discovery (1995) 172-178, 949-982 (Manfred E. Wolff, Ed., 5th edition) and J. Rautio's Prodrugs and Targeted Delivery (2011) 31-60 (Wiley-VCH, Methods and Principles in Medicinal Chemistry Volume 47) and G. Thomas's Fundamentals of Medicinal Chemistry (2003) 195-200 (Wiley).

In the compounds of the present invention, triptolide derivatives have the stereochemistry shown by the structural formulas of general formula I (there are ten chiral centers, nine of which being derived from triptolide, and one being derived from amino acid); and general formula II (there are eleven chiral centers, nine of which being derived from triptolide, and two being derived from amino acid). The definition and convention of the stereochemistry used herein generally follow McGraw-Hill Dictionary of Chemical Terms (S. P. Parker, Ed., McGraw-Hill Book Company, New York, 1984); Eliel, E. and Wilen, S., Stereochemistry of Organic Compounds (John Wiley & Sons, Inc., New York, 1994). Many organic compounds exist in optically active forms, that is they have the ability to rotate the plane of plane-polarized light.

The term "treatment" used herein generally refers to obtaining a desired pharmacological and/or physiological effect. The effect may be prophylactic in terms of completely or partially preventing a disease or a symptom thereof; and/or may be therapeutic in terms of a partial or complete stabilization or cure for a disease and/or an adverse effect caused by the disease. The "treatment" used herein encompasses any treatment of a disease in a patient, including: (a) preventing a disease or a symptom, which the disease or the symptom occurs in a patient that have not yet been diagnosed with the disease; (b) inhibiting the symptom of a disease, i.e. arresting the development of the symptom; or (c) relieving the symptom of a disease, i.e. causing regression of the disease or the symptom.

The compounds of the present invention may be prepared according to conventional organic chemical synthesis methods. For example, a general method of preparing the compound of general formula (I) of the present invention is as follows:

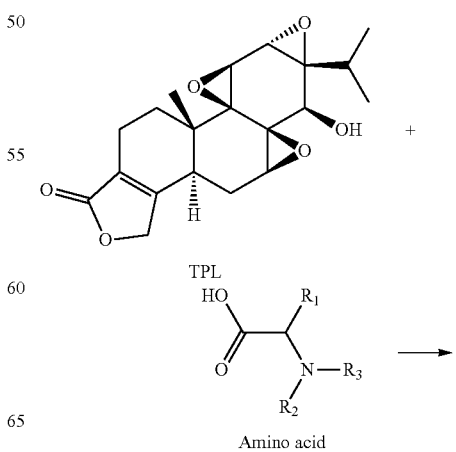

-continued

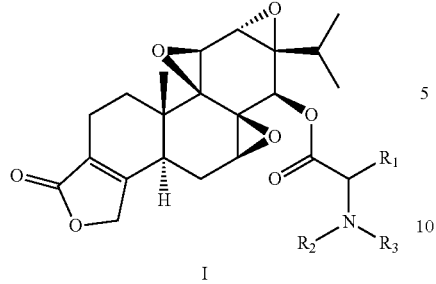

I

The C14-hydroxyl esterified amino acid derivative of triptolide with single amino acid esterification of general formula (I) may be obtained through the esterification condensation of naturally extracted and isolated triptolide (TPL) with respective amino acids $R_2R_3NCHR_1CO_2H$ in the presence of a condensing agent or catalyst in a suitable solvent at an appropriate temperature; and may also be obtained through the esterification condensation of triptolide with respective amino acid acyl chlorides $R_2R_3NCHR_1COCl$ in the presence of a basic agent; or through the activation of amino acid $R_2R_3NCHR_1CO_2H$ to generate an active ester intermediate, which then reacted with triptolide to generate the C14-hydroxyl esterified amino acid derivative of triptolide (I); and may also through the activation of amino acid $R_2R_3NCHR_1CO_2H$ to generate a mixed anhydride intermediate, which then reacted with triptolide to generate the C14-hydroxyl esterified amino acid derivative of triptolide (I). $R_1$, $R_2$, $R_3$ in the formula (I), $R_1$, $R_2$, $R_3$ in the amino acid $R_2R_3NCHR_1CO_2H$, $R_1$, $R_2$, $R_3$ in the amino acid acyl chloride $R_2R_3NCHR_1COCl$, $R_1$, $R_2$, $R_3$ in the active ester intermediate, and $R_1$, $R_2$, $R_3$ in the mixed anhydride intermediate all have the same definitions as those in the formula (I) above.

A general method of preparing the compound of general formula (II) of the present invention is as follows:

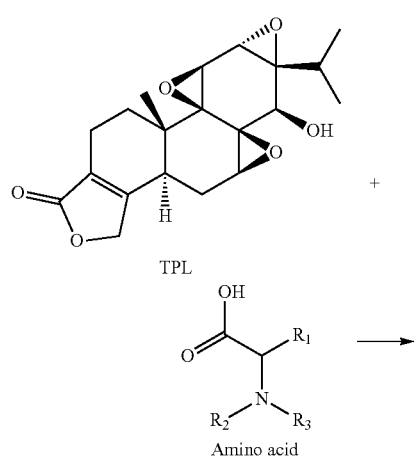

TPL

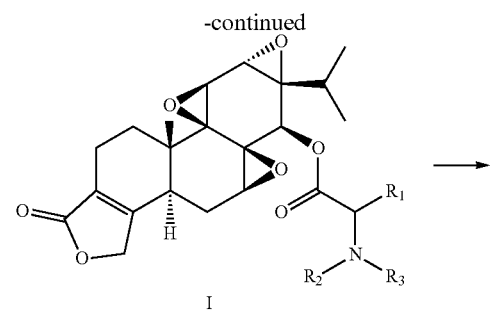

I

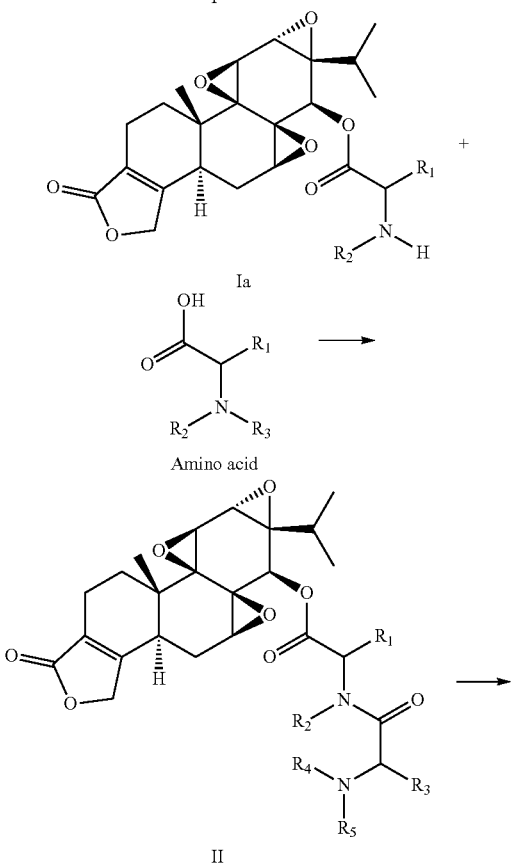

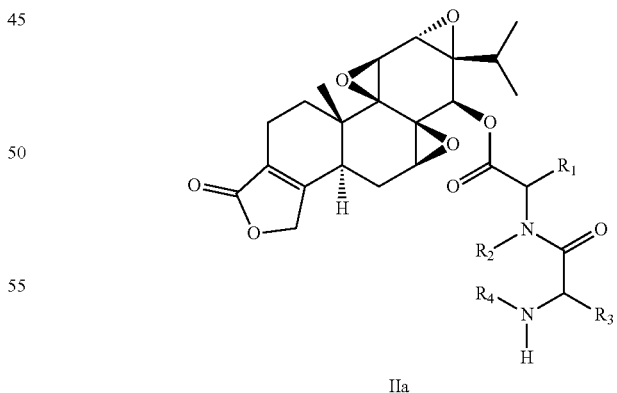

IIa

The C14-hydroxyl esterified amino acid derivative of triptolide with dipeptide esterification (II) may be prepared by first preparing the C14-hydroxyl esterified amino acid derivative of triptolide (I) according to the foregoing method, wherein in the amino acid $R_2R_3NCHR_1CO_2H$ used, $R_2$ or $R_3$ is a protecting group. The amino-protecting groups are known to those skilled in the art, and can be easily found in literature resources, for example, Greene and Wuts, "Protective Groups in Organic Synthesis," 3rd edition, John Wiley & Sons Press, New York, N.Y., 1999, the entirety of which is incorporated herein by reference. Then, the protecting group is removed to obtain a derivative of general formula Ia, which is further subjected to amidation condensation with respective amino acids $R_5R_6NCHR_4CO_2H$ in the presence of a condensing agent or catalyst in a suitable solvent at an appropriate temperature, to generate the C14-hydroxyl esterified amino acid derivative of triptolide with dipeptide esterification (II); and the derivative of general formula Ia obtained by the removal of the protecting group may also be subjected to amidation condensation with respective amino acid acyl chlorides $R_5R_6NCHR_4COCl$ in the presence of a basic agent, to generate the C14-hydroxyl esterified amino acid derivative of triptolide with dipeptide esterification (II); or the C14-hydroxyl esterified amino acid derivative of triptolide with dipeptide esterification (II) may be generated through the activation of amino acid $R_5R_6NCHR_4CO_2H$ to generate an active ester intermediate, which then reacted with the C14-hydroxyl esterified amino acid derivative of triptolide (Ia); and may also be generated through the activation of amino acid $R_5R_6NCHR_4CO_2H$ to generate a mixed anhydride intermediate, which then reacted with the C14-hydroxyl esterified amino acid derivative of triptolide (Ia). When $R_5$ and $R_6$ are protecting groups, a compound IIa may be obtained by further removing the protecting groups. $R_1$, $R_2$, $R_3$, $R_4$, $R_5$ and $R_6$ in the formula (II), $R_1$, $R_2$, $R_3$ in the amino acid $R_2R_3NCHR_1CO_4H$, $R_1$, $R_2$, $R_3$ in the amino acid acyl chloride $R_2R_5NCHR_6COCl$, $R_1$, $R_2$, $R_3$ in the active ester intermediate, and $R_1$, $R_2$, $R_3$ in the mixed anhydride intermediate all have the same definitions as those in the formula (II) above. $R_4$, $R_5$, $R_6$ in the amino acid $R_5R_6NCHR_4CO_2H$, $R_4$, $R_5$, $R_6$ in the amino acid acyl chloride $R_5R_6NCHR_4COCl$, and $R_4$, $R_5$, $R_6$ in the mixed anhydride intermediate all have the same definitions as those in the formula (II) above.

The reactions described above are generally performed in the presence of a base or basic agent. The base herein may be, but is not limited to, an organic base. For example, it may be diisopropylethylamine, triethylamine, or dimethylaminopyridine.

The reactions described above are generally performed in a solvent. The solvent used includes, but is not limited to, an aprotic polar solvent, e.g. dichloromethane (DCM), dimethyl sulfoxide (DMSO), dimethyl formamide (DMF), dimethyl acetamide (DMA), N-methypyrrole (NMP), or tetrahydrofuran (THF), or the like.

The reaction temperature of the reactions described above is generally 0° C. to 50° C. The reaction temperature generally varies with different raw materials and bases used in the reactions.

The raw material of the preparation reactions is triptolide (TPL). The raw material is extracted and isolated from a natural product, and is commercially available.

The organic acids, organic anhydrides or organic acyl chlorides used in the preparation reactions are all commercially available.

Conventional chemical conversions may be used in implementing the present invention. Those skilled in the art may determine appropriate chemical reagents, solvents, protecting groups, and reaction conditions for these chemical conversions. Related information is described in R. Larock, Comprehensive Organic Transformations, VCH publisher (1989); T. W. Greene and P. G. M. Wuts, Protective Groups in Organic Synthesis, 3rd edition, John Wiley and Sons (1999); L. Fieser and M. Fieser, Fieser and Fieser's Reagents for Organic Synthesis, John Wiley and Sons (1994); and Encyclopedia of Reagents for Organic Synthesis, L. Paquette Ed., John Wiley and Sons (1995) and later versions.

Protecting groups refer to those groups that once being attached to active moieties (e.g. hydroxyl or amino), the protecting groups prevent these moieties from being interfered by the subsequent reaction, and can be removed by conventional methods after the reaction. Examples of a hydroxyl-protecting group include, but are not limited to, alkyl, benzyl, allyl, trityl (i.e. triphenylmethyl), acyl (e.g. benzoyl, acetyl or HOOC—X"—CO—, X" being alkylene, alkenylene, cycloalkylene or arylene), silyl (e.g. trimethylsilyl, triethylsilyl and t-butyldimethylsilyl), alkoxycarbonyl, aminocarbonyl (e.g. dimethylaminocarbonyl, methylethylaminocarbonyl and phenylaminocarbonyl), alkoxymethyl, benzyloxymethyl, and alkyl mercaptomethyl. Examples of an amino-protecting group include, but are not limited to, alkoxycarbonyl, alkanoyl, aryloxycarbonyl, aryl-substituted alkyl, and the like. Hydroxyl- and amino-protecting groups have been discussed in T. W. Greene and P. G. M. Wuts, Protective Groups in Organic Synthesis, 2nd edition, John Wiley and Sons (1991). Both hydroxyl- and amino-protecting groups can be removed by conventional methods after the reaction.

The present invention also provides a pharmaceutical composition comprising the compound of general formula I/general formula II of the present invention.

The present invention also provides a pharmaceutical composition comprising at least one compound of formula I or formula II of the present invention as described above, and an optional pharmaceutically acceptable excipient.

Methods of preparing various pharmaceutical compositions containing a certain amount of an active ingredient are known, or are apparent in light of this disclosure, to those skilled in the art, as described in Remington's Pharmaceutical Sciences, Martin, E. W., ed., Mack Publishing Company, 19th ed. (1995). The methods of preparing said pharmaceutical compositions comprise incorporating an appropriate pharmaceutical excipient, carrier, diluent, etc.

The pharmaceutical formulations of the present invention are made with known methods, including conventional mixing, dissolution or lyophilization method.

The compounds of the present invention may be prepared as a pharmaceutical composition, and administered to a patient in various routes suitable for a selected mode of administration, for example, orally or parenterally (via an intravenous, intramuscular, local, or subcutaneous route).

Thus, the compounds of the present invention may be administered systemically, for example, orally, in conjunction with a pharmaceutically acceptable carrier (e.g., an inert diluent or assimilable edible carrier). They may be encapsulated in a hard or soft gelatin capsule, and may be pressed into a tablet. For oral administration, active compounds may be combined with one or more excipients, and used in the form of swallowable tablets, buccal tablets, lozenges, capsules, elixirs, suspensions, syrups, discs, and the like. Such compositions and formulations should comprise at least 0.01% of an active compound. Of course, the ratio of such compositions and formulations may vary, and may be comprised from about 0.1% to about 99% of the weight of the given unit dosage form. The amount of an active compound in this therapeutically useful composition is such that an effective dose level will be obtained.

Tablets, lozenges, pills, capsules and the like may also comprise: binder, such as tragacanth, arabic gum, corn starch, or gelatin; excipient, such as dibasic calcium phosphate; disintegrant, such as corn starch, potato starch, alginic acid, and the like; lubricant, such as magnesium stearate; and sweetener, such as sucrose, fructose, lactose, or aspartame; or flavoring agent, such as mint, wintergreen oil or cherry flavoring. When the unit dosage form is a capsule, in addition to the types of materials above, it may also comprise a liquid carrier, such as vegetable oil or polyethylene glycol. Various other materials may present as coatings or to otherwise modify the physical form of the solid unit dosage form. For example, tablets, pills or capsules may be coated with gelatin, wax, shellac, or sugar and the like. A syrup or elixir may comprise an active compound, sucrose or fructose as a sweetener, methyl or propyl parahydroxybenzoate as a preservative, a dye and a flavoring agent (such as cherry or orange flavor). Of course, any material used in preparing any unit dosage form should be pharmaceutically acceptable and substantially non-toxic in the amounts applied. In addition, the active compound may be incorporated into sustained-release formulations and devices.

The active compound may also be administered intravenously or intraperitoneally by infusion or injection. An aqueous solution of the active compound or salts thereof may be prepared, optionally mixed with a non-toxic surfactant. Alternatively, a dispersion in glycerol, liquid polyethylene glycol, triacetin, and a mixture thereof and in oil may be prepared. Under ordinary conditions of storage and use, these formulations comprise preservatives to prevent the growth of microorganisms.

The pharmaceutical dosage forms suitable for injection or infusion may include a sterile aqueous solution or dispersion or sterile powders comprising active ingredients (optionally encapsulated in liposomes), which are adapted for the extemporaneous preparation of sterile injectable or infusible solution or dispersion. In all cases, the final dosage form must be sterile, liquid and stable under the conditions of manufacture and storage. The liquid carrier may be a solvent or liquid dispersion medium, including, for example, water, ethanol, a polyol (e.g. glycerol, propylene glycol, liquid polyethylene glycol, and the like), vegetable oil, non-toxic glyceride, and suitable mixtures thereof. The proper fluidity may be maintained, for example, by the formation of liposomes, by the maintenance of the desired particle size in the case of dispersion, or by the use of a surfactant. The prevention of microorganisms can be brought about by various antibacterial agents and antifungal agents (such as parabens, chlorobutanol, phenol, sorbic acid, thiomersal, and the like). In many cases, it is preferable to include isotonic agents, such as sugar, buffers or sodium chloride. Prolonged absorption of the injectable composition may be brought about by the use of a composition of agents for delaying absorption (for example, aluminum monostearate and gelatin).

A sterile injectable solution may be prepared by incorporating a required amount of the active compound in a suitable solvent with a variety of other ingredients listed above, as required, followed by sterilization by filtration. In the case of sterile powders used to prepare a sterile injection solution, the preferred methods of preparation are vacuum drying and freeze-drying, which produces a powder of the active ingredient plus any additional desired ingredient presented in a previous sterile-filtered solution.

Useful solid carriers include finely divided solids (such as talc, clay, microcrystalline cellulose, silica, alumina, and the like). Useful liquid carriers include water, ethanol or glycol or a water-ethanol/glycol mixture, in which the present compounds can be dissolved or dispersed at an effective content, optionally with the aid of a non-toxic surfactant. An adjuvant, such as a flavoring, and an additional antimicrobial agent may be added to optimize the properties for a given use.

A thickener (such as synthetic ploymers, fatty acids, fatty acid salts and esters, fatty alcohols, modified celluloses or modified inorganic materials) may also be used with a liquid carrier to form a coatable paste, gel, ointment, soap, and the like, for application directly to the skin of a user.

The amount of the compound, or an active salt or derivative thereof, required for use in treatment will vary depending not only on the particular active ingredient selected but also on the route of administration, the nature of the disease to be treated, and the age and condition of the patient, and will ultimately depend on the discretion of the attendant physician or clinician.

The above formulation may be present in a unit dosage form, which is a physically discrete unit containing a unit dose, suitable for administration in human or other mammals. The unit dosage form may be a capsule or a tablet, or a number of capsules or tablets. The quantity of the active ingredient in a unit dose may be varied or adjusted from about 0.01 to about 1000 milligrams or more according to the particular treatment involved.

In the following examples, the present invention will be explained in more detail. It should be understood, however, that the following examples are intended to illustrate the invention without limiting the scope of the invention in any way.

DETAILED DESCRIPTION OF THE INVENTION

Figure 1:
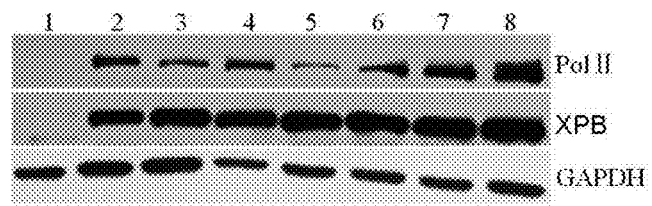
FIG. 1 shows the results of the immunoblot analysis of XPB and Pol II protein levels in tumor cells and normal cells.

The chemical raw materials used in the following examples are all commercially available or obtained by the synthesis methods well known in the art.

EXAMPLE 1

Synthesis and Identification of Compound 14-D-Valine-TPL (14-Dextro-Valine-Triptolide)

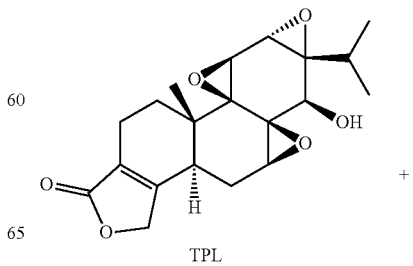

TPL

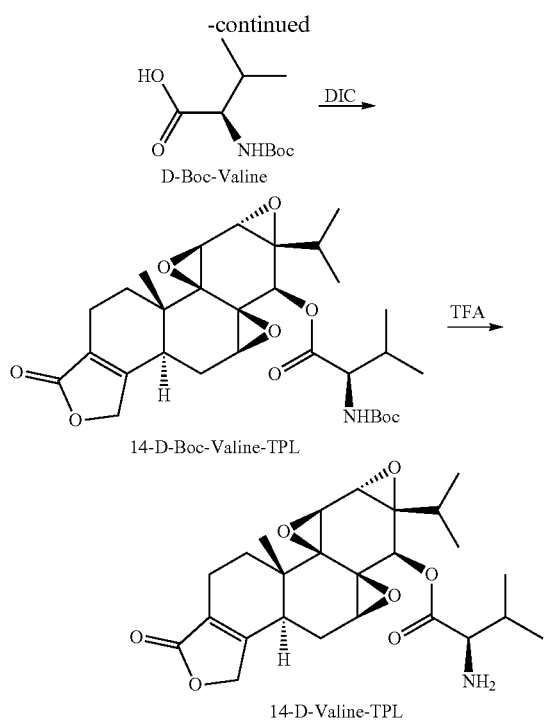

EXAMPLE 2

Synthesis and Identification of Compound 14-L-Valine-D-Valine-TPL (14-Levo-Valine-Dextro-Valine-Triptolide)

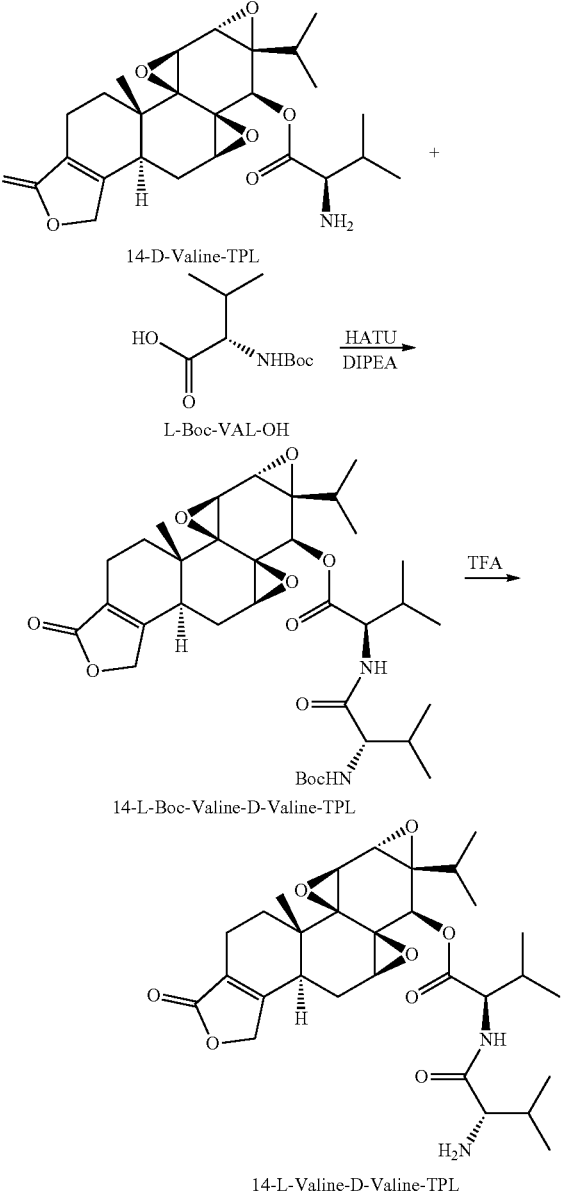

In the scheme, TPL: triptolide; D-Boc-Valine: Dextro-(N-Boc)-Valine; DIC: N,N'-diisopropylcarbodiimide; DMAP: 4-dimethylaminopyridine; DCM: dichloromethane; TFA: trifluoroacetic acid.

Step 1: Triptolide TPL (500 mg, 1.39 mmol, 1.0 eq.) and Dextro-(N-Boc)-Valine (1500 mg, 6.91 mmol, 5 eq.) were dissolved in dichloromethane (20 mL), and cooled to 0° C. N,N'-diisopropylcarbodiimide (4 mL, 13 mmol, 9.35 eq.) and 4-dimethylaminopyridine (130 mg, 1.07 mmol, 0.8 eq.) were added into the mixed solution at 0° C., and reacted for 24 hours at 25° C. The reaction solution was diluted with ethyl acetate and washed with water, and then washed with saturated ammonium chloride, dried and concentrated to give a crude product. The crude product was purified on a preparative silica gel column to produce D-Boc-Valine-TPL (14-Dextro-Boc-Valine-Triptolide) as a white solid (250 mg), with a yield of 32.2%.

Step 2: The product D-Boc-Valine-TPL (14-D-Boc-Valine-Triptolide) (200 mg) in the previous step was dissolved in dichloromethane (15 mL), and 3 mL of trifluoroacetic acid was added dropwise. After the addition, the reaction solution was reacted at 25° C. for 3.5 hours. The reaction solution was diluted with dichloromethane and washed with an aqueous sodium bicarbonate solution, and then dried and concentrated to give a crude product. The crude product was purified by preparative high-performance liquid chromatography to produce D-Valine-TPL (14-Detxtro-Valine-Triptolide) as a white solid (120 mg), with a yield of 73%.

LC-MS: Retention time: 0.83 min (UV220: 97.8%), m/z: 460.28 (M+H). 1H NMR (400 MHz, CDCl3) δ 5.11 (s, 1H), 4.78-4.62 (m, 2H), 4.01 (s, 1H), 3.86 (d, J=2.7 Hz, 1H), 3.58 (d, J=2.4 Hz, 1H), 3.52 (d, J=4.8 Hz, 1H), 2.72 (d, J=11.9 Hz, 1H), 2.47 (s, 1H), 2.33 (d, J=16.3 Hz, 1H), 2.26-2.08 (m, 2H), 1.94 (dd, J=36.2, 22.1 Hz, 2H), 1.58 (dd, J=12.0, 4.5 Hz, 1H), 1.23 (d, J=5.6 Hz, 4H), 1.16 (d, J=4.8 Hz, 3H), 1.03 (s, 3H), 0.93 (d, J=6.4 Hz, 3H), 0.81 (d, J=6.5 Hz, 3H).

In the scheme, D-Valine-TPL: 14-Dextro-Valine-Triptolide; L-Boc-Valine: Levo-(N-Boc)-Valine; HATU: 2-(7-aza-benzotriazole)-N,N,N',N'-tetramethyluronium hexafluorophosphate; DIPEA: N,N-diisopropylethylamine; DCM: dichloromethane; TFA: trifluoroacetic acid.

Step 1: D-Valine-TPL (14-Dextro-Valine-Triptolide) (110 mg, Example 1) and Levo-(N-Boc)-Valine (1.2 eq.) were dissolved in dichloromethane (10 mL), and HATU (2-(7-aza-benzotriazole)-N,N,N',N'-tetramethyluronium hexafluorophosphate, 1.5 eq.) and DIPEA (N,N-diisopropylethylamine, 2 eq.) were added into the mixed solution, and reacted at 25° C. for half an hour. The reaction solution was washed with a 1M potassium carbonate solution, and dried and concentrated to give a crude product. The crude product was purified on a preparative silica gel column to produce 14-L-Boc-Valine-D-Valine-TPL (14-Levo-(N-Boc)-Valine-Dextro-Valine-Triptolide) as a white solid (85 mg).

Step 2: The product 14-L-Boc-Valine-D-Valine-TPL (14-Levo-(N-Boc)-Valine-Dextro-Valine-Triptolide) (85 mg) in the previous step was dissolved in dichloromethane (5 mL), and 1 mL of trifluoroacetic acid was added dropwise. After the addition, the reaction solution was reacted at 25° C. for 3.5 hours. The reaction solution was diluted with dichloromethane and washed with an aqueous sodium bicarbonate solution, and then dried and concentrated to give a crude product. The crude product was purified by preparative high-performance liquid chromatography to produce 14-L-Valine-D-Valine-TPL (14-Levo-Valine-Dextro-Valine-Triptolide) as a white solid (51.5 mg).

LC-MS: Retention time: 0.96 min (UV220: 97.7%), m/z: 559.44 (M+H). 1H NMR (400 MHz, CDCl3) δ 7.52 (d, J=7.8 Hz, 1H), 5.60 (b, 3H), 5.06 (s, 1H), 4.80-4.65 (m, 2H), 4.58 (dd, J=7.8, 4.0 Hz, 1H), 4.20 (s, 1H), 3.88 (d, J=2.7 Hz, 1H), 3.57 (d, J=2.2 Hz, 1H), 3.50 (d, J=5.3 Hz, 1H), 2.72 (d, J=11.7 Hz, 1H), 2.47-2.09 (m, 5H), 1.92 (dd, J=17.9, 10.2 Hz, 2H), 1.57 (dd, J=11.5, 5.1 Hz, 1H), 1.25 (dd, J=12.2, 5.5 Hz, 2H), 1.13-1.04 (m, 11H), 1.02 (s, 3H), 0.92 (t, J=8.4 Hz, 3H), 0.83 (d, J=6.7 Hz, 3H).

EXAMPLE 3

Synthesis and Identification of Compound 14-L-Valine-TPL (14-Levo-Valine-Triptolide)

The compound 14-L-Valine-TPL (14-Levo-Valine-Triptolide) was synthesized following the method in Example 1, while replacing D-Boc-Valine-TPL (Dextro-N-Boc-Valine) with L-Boc-Valine (Levo-N-Boc-Valine).

LC-MS: Retention time: 0.96 min (UV220, 100%), m/z: 460.28 (M+H). 1H NMR (300 MHz, CDCl3) δ 5.10 (d, J=5.4 Hz, 1H), 4.73-4.60 (m, 2H), 3.99 (s, 1H), 3.91-3.79 (m, 1H), 3.63-3.44 (m, 2H), 2.67 (s, 1H), 2.55-1.79 (m, 7H), 1.65-1.47 (m, 1H), 1.31-1.09 (m, 7H), 1.01 (s, 3H), 0.97-0.86 (m, 3H), 0.85-0.72 (m, 3H).

EXAMPLE 4

Synthesis and Identification of Compound 14-L-Valine-L-Valine-TPL (14-Levo-Valine-Levo-Valine-Triptolide)

The compound 14-L-Valine-L-Valine-TPL (14-Levo-Valine-Levo-Valine-Triptolide) was synthesized following the method in Example 2, while replacing 14-D-Valine-TPL (14-Dextro-Valine-Triptolide, Example 1) with 14-L-Valine-TPL (14-Levo-Valine-Triptolide, Example 3), and replacing D-Boc-Valine-TPL (Dextro-N-Boc-Valine) with L-Boc-Valine (Levo-N-Boc-Valine).

LC-MS: Retention time: 1.78 min (ELSD: 99.6%), m/z: 559.50 (M+H). 1H NMR (400 MHz, CDCl3) δ 7.83 (s, 1H), 5.08 (d, J=7.5 Hz, 1H), 4.75-4.65 (m, 2H), 4.57 (dd, J=8.7, 4.7 Hz, 1H), 3.84 (dd, J=5.8, 3.2 Hz, 1H), 3.53 (ddd, J=17.4, 11.7, 4.1 Hz, 2H), 2.70 (s, 1H), 2.43-2.27 (m, 3H), 2.23-2.12 (m, 2H), 2.04-1.88 (m, 2H), 1.67-1.54 (m, 1H), 1.30-1.20 (m, 1H), 1.12-0.99 (m, 10H), 0.95 (t, J=7.5 Hz, 5H), 0.90-0.77 (m, 3H).

EXAMPLE 5

Synthesis and Identification of Compound 14-D-Valine-D-Valine-TPL (14-Dextro-Valine-Dextro-Valine-Triptolide)

The compound 14-D-Valine-D-Valine-TPL (14-Dextro-Valine-Dextro-Valine-Triptolide) was synthesized following the method in Example 2, while replacing L-Boc-Valine-TPL (Levo-N-Boc-Valine) with D-Boc-Valine (Dextro-N-Boc-Valine).

LC-MS: Retention time: 1.95 min (ELSD: 98.0%), m/z: 559.50 (M+H). 1H NMR (400 MHz, CDCl3) δ 7.81 (d, J=8.8 Hz, 1H), 5.08 (s, 1H), 4.69 (s, 2H), 4.61 (dd, J=8.8, 4.5 Hz, 1H), 3.84 (d, J=3.2 Hz, 1H), 3.57 (d, J=2.7 Hz, 1H), 3.49 (d, J=5.8 Hz, 2H), 2.74-2.68 (m, 1H), 2.39-2.27 (m, 3H), 2.22-2.10 (m, 2H), 1.94 (ddd, J=25.7, 16.2, 10.6 Hz, 2H), 1.59 (dd, J=12.4, 4.6 Hz, 1H), 1.28-1.20 (m, 1H), 1.06 (dt, J=12.6, 6.1 Hz, 12H), 0.95 (dd, J=12.7, 6.9 Hz, 6H), 0.85 (d, J=6.9 Hz, 3H).

EXAMPLE 6

Synthesis and Identification of Compound 14-L-Phenylalanyl-L-Tyrosine-TPL (14-Levo-Phenylalanyl-Levo-Tyrosine-Triptolide)

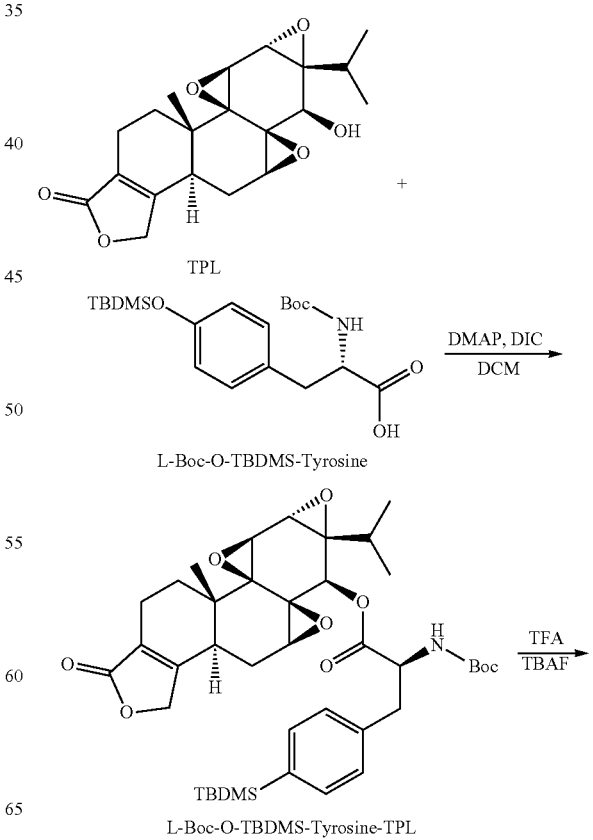

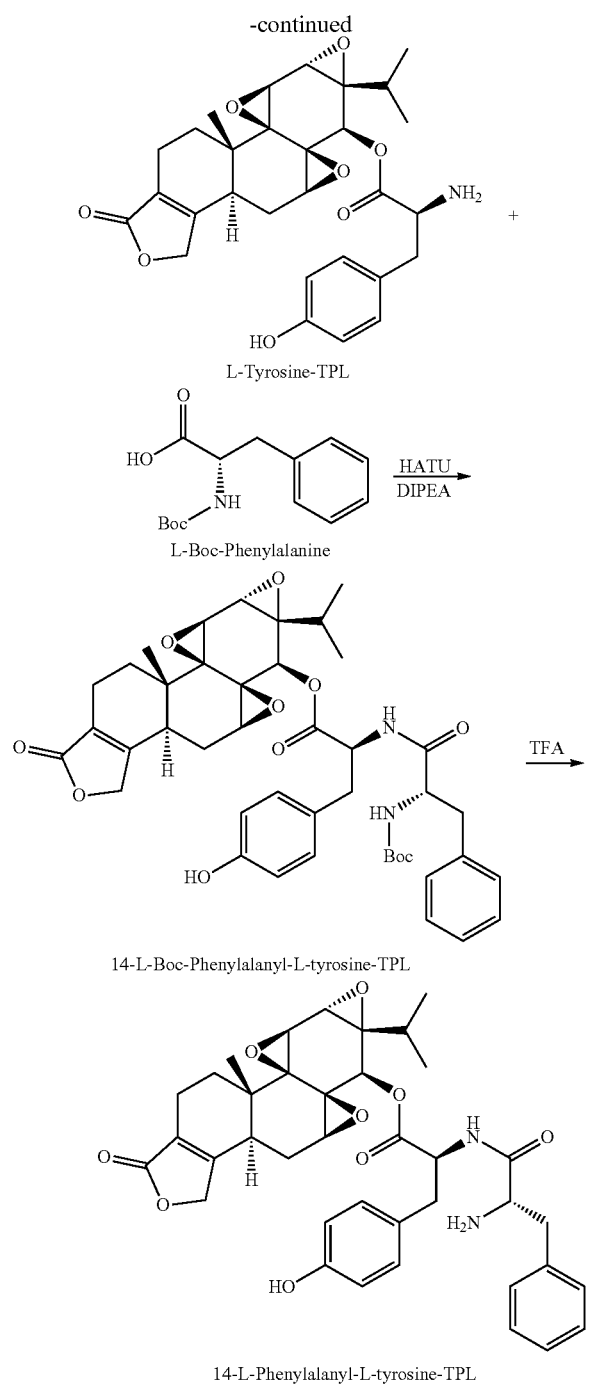

In the scheme, TPL: triptolide; L-Boc-O-TBDMS-Tyrosine: Levo-(N-Boc-O-t-butyldimethyllsilyl)-Tyrosine; DIC: N,N'-diisopropylcarbodiimide; DMAP: 4-dimethylaminopyridine; DCM: dichloromethane; TFA: trifluoroacetic acid. TBAF: tetrabutylammonium fluoride;

D-Valine-TPL: 14-Dextro-Valine-Triptolide; L-Boc-Phenylalanine: Levo-(N-Boc)-Phenylalanine; HATU: 2-(7-azabenzotriazole)-N,N,N',N'-tetramethyluronium hexafluorophosphate; DIPEA: N,N-diisopropylethylamine;

Compound L-Tyrosine-TPL (14-Levo-Tyrosine-Triptolide) was synthesized following the method in Example 1, while replacing D-Boc-Valine-TPL (Dextro-N-Boc-Valine) with L-Boc-O-TBDMS-Tyrosine: Levo-(N-Boc-O-t-butyldimethyllsilyl)-Tyrosine.

The compound 14-L-Phenylalanyl-L-tyrosine-TPL (14-Levo-Phenylalanyl-Levo-tyrosine-Triptolide) was synthesized following the method in Example 2, while replacing 14-D-Valine-TPL (14-Dextro-Valine-Triptolide, Example 1) with the compound L-Tyrosine-TPL (14-Levo-Tyrosine-Triptolide), and replacing D-Boc-Valine-TPL (Dextro-N-Boc-Valine) with L-Boc-Phenylalanine (Levo-(N-Boc)-Phenylalanine).

LC-MS: Retention time: 1.06 min (UV220: 97.8.0%), m/z: 671.56 (M+H). 1H NMR (400 MHz, DMSO) δ 9.34 (s, 0H), 9.17 (s, 0H), 8.07 (d, J=15.1 Hz, 1H), 7.42-7.14 (m, 2H), 7.13-7.03 (m, 1H), 6.89 (d, J=7.6 Hz, 0H), 6.74-6.62 (m, 1H), 5.01 (d, J=6.3 Hz, 0H), 4.82 (d, J=17.7 Hz, 1H), 4.64-4.58 (m, 0H), 4.03 (d, J=3.2 Hz, 1H), 3.94 (d, J=3.2 Hz, 0H), 3.25 (d, J=14.2 Hz, 0H), 3.15 (s, 0H), 3.05 (dd, J=13.9, 6.2 Hz, 0H), 2.94-2.77 (m, 1H), 2.64 (s, 1H), 2.31-2.07 (m, 1H), 1.92 (d, J=24.5 Hz, 1H), 1.87-1.72 (m, 1H), 1.66-1.53 (m, 1H), 1.38-1.17 (m, 1H), 1.04 (d, J=6.8 Hz, 0H), 0.97-0.88 (m, 2H), 0.80 (dd, J=6.7, 3.8 Hz, 1H), 0.65 (d, J=6.8 Hz, 3H).

EXAMPLE 7

Comparison of Therapeutic Windows Between the Compound 14-D-Valine-TPL of the Invention and Triptolide (TPL)

(1) Experimental Materials

Leukemia cell strains: Sup-B15 (Ph+acute lymphoblastic leukemia), CEM (acute lymphoblastic leukemia, ALL), and Molt-4 (acute lymphoblastic leukemia, ALL). Normal blood cell samples: peripheral blood from healthy volunteers.
Primary reagent: 14-D-Valine-TPL of the invention. Primary instruments: cell incubator and microplate reader.

(2) Experimental Method 5000 well-grown leukemia cells or normal human blood cells were taken and seeded into wells of a 96-well cell culture plate. The medium was 1640 cell medium containing 10% fetal bovine serum. 14-D-Valine-TPL with different concentrations was added, and after being uniformly mixed, the plate was placed in a carbon dioxide (5% CO2) cell incubator, and incubated at 37° C. for 72 hours. The concentration of live cells was then determined using the MTT assay. In this experiment, the cell viability in the control group (without the compound treatment) was set to be 100%, and the cell viability (%) after the action of the compound the half maximal growth inhibitory concentration of leukemia cells at 72 hours (IC50 value at 72 hours) and the therapeutic window index were calculated. Therapeutic window index=IC50 value of normal blood cells/IC50 value of leukemia cells. The therapeutic window index of < or =1 indicates that there is no therapeutic window, and the compound is non-selective with the same toxicity to normal cells and tumor cells. The therapeutic window index of >1 indicates that there is a therapeutic window, and the compound is more toxic to tumor cells than to normal cells. A larger therapeutic window indicates a better selectivity of the compound for tumor cells.

(3) Experimental Results

The experimental results are shown in Table 1, which indicates that the compound 14-D-Valine-TPL of the invention has a better therapeutic window, while triptolide has substantially no therapeutic window. Table 1 shows that triptolide (TPL) had a small therapeutic window (2.0) only for Molt-4 cells, while its therapeutic windows for other 3 leukemia cells, Jurkat, CEM and Sup-B15, were all <1, which were 0.64, 0.93 and 0.94, respectively. These indicates that triptolide has substantially no selectivity for normal cells and tumor cells, which is consistent with the result reported in the literatures that TPL has substantially no therapeutic window. In contrast, 14-D-Valine-TPL of the invention has therapeutic window indices of 5.54-18.58 for 4 different types of human leukemia cells that have been assayed, indicting that 14-D-Valine-TPL has a larger therapeutic window for all 4 types of leukemia, with a therapeutic window index for Molt-4 cells being up to 18.58.

TABLE 1

Comparison of the therapeutic windows between 14-D-Valine-TPL and triptolide (TPL)

|  | 14-D-Valine-TPL | | TPL | |
|---|---|---|---|---|
|  | IC50 (nM/L) | Therapeutic window | IC50 | Therapeutic window |
| Leukemia Cell Line | | | | |
| Jurkat | 36.301 | 5.54 | 33.829 | 0.64 |
| CEM | 25.488 | 7.89 | 23.286 | 0.93 |
| Molt-4 | 10.824 | 18.58 | 10.718 | 2.03 |
| Sup-B15 | 20.674 | 9.73 | 23.153 | 0.94 |
| Normal Blood Cell | | | | |
| No1 | 202.706 | | 29.289 | |
| No2 | 198.826 | | 20.772 | |
| No3 | 205.784 | | 9.383 | |
| No4 | 199.835 | | 8.968 | |
| No5 | 213.719 | | 20.072 | |
| No6 | 189.872 | | 20.445 | |
| No7 | 203.546 | | 19.515 | |
| No8 | 184.509 | | 9.710 | |
| No9 | 210.835 | | 57.443 | |
| Overall | 201.07 | | 21.733 | |

EXAMPLE 8

Determination of in vitro Activity of the Compound 14-D-Valine-TPL of the Invention Against Leukemia (1) Experimental Materials Leukemia cell strains: human KG-1a (acute myelogenous leukemia, AML-MO), THP-1 (acute myelogenous leukemia, AML-M5), NB4 (acute promyelocytic leukemia, AML), Kasumi-1 (acute myelogenous leukemia M2 type, AML-M2), KG-1 (acute myelogenous leukemia, AML), Jurkat (acute lymphoblastic leukemia, ALL), and H9 (acute lymphoblastic leukemia, ALL).

Primary reagent: 14-D-Valine-TPL of the invention. Primary instruments: cell incubator and microplate reader.

(2) Experimental Method 5000 well-grown leukemia cells were taken and seeded into wells of a 96-well cell culture plate. The medium was 1640 cell medium containing 10% fetal bovine serum. 14-D-Valine-TPL with different concentrations was added, and after being uniformly mixed, the plate was placed in a carbon dioxide (5% $CO_2$) cell incubator, and incubated at 37° C. for 72 hours. The concentration of live cells was then determined using the MTT assay. In this experiment, the cell viability in the control group (without the compound treatment) was set to be 100%, and the cell viability (%) after the action of the compound and the half maximal growth inhibitory concentration of leukemia cells at 72 hours ($IC_{50}$ value at 72 hours) were calculated.

(3) Experimental Results

Experimental results are shown in Table 2. Table 2 shows that 14-D-Valine-TPL of the invention can induce the death of human acute myelogenous leukemia cells and acute lymphoblastic leukemia cells, and inhibit the growth of these leukemia cells.

TABLE 2

Inhibitory effects of the derivatives of the invention on the growth of different types of leukemia cells

| Cell Line | 14-D-Val-TPL IC50 (nM/L) | 14-L-Val-TPL IC50 (nM/L) | 14-L-Val-14-L-Val-TPL IC50 (nM/L) |
|---|---|---|---|
| KG-1 | 49.0 | 8.86 | |
| KG-1a | 31.0 | | 20 |
| THP-1 | 16.0 | 5.0 | |
| HL-60 | 65.8 | | |
| U937 | 60.0 | | |
| Jurkat | 36.301 | | |
| CEM | 25.488 | | |
| Molt-4 | 10.824 | | |
| Sup-B15 | 20.674 | | |

EXAMPLE 9

Determination of in vivo Activity of the Compound 14-D-Valine-TPL of the Invention Against Human Leukemia in Mice (1) Experimental Materials Experiment animal: NOD/SCID mice obtained from the Shanghai Animal Center of the Chinese Academy of Sciences (CAS).

Leukemia cell strains: human KG-1a (acute myelogenous leukemia, AML-MO), and THP-1 (acute monocytic leukemia, AML-M5), obtained from ATCC Library.

Reagent: 14-D-Valine-TPL trifluoroacetate of the invention, dissolved with sterile PBS to a concentration of 10 mg/ml, and then diluted with sterile deionized water to a required working concentration.

Primary instruments: cell incubator and microplate reader.

(2) Experimental Method 7-week old female NOD/SCID mice were taken and inoculated subcutaneously with $1\times10^7$ cells (0.2 ml) per mouse in axilla, with human acute myelogenous leukemia KG-1a cells on the left and human acute monocytic leukemia THP-1 cells on the right. When tumors grew to a tumor size of around 0.5 cm, the mice were randomized into groups with 3 mice each. An equivalent amount of PBS was used for the control group, and the 14-D-Valine-TPL group was divided into two groups with 0.2 mg/kg body weight and 0.4 mg/kg body weight: intragastric administration 2 times a day (one at 8 a.m. and one at 4 p.m.) for consecutive 14 days of treatment. An observation was made for total 30 days, during which the conditions of the mice such as tumor size, weight, activity, diet, and the like were measured. At the end of the experiment, the mice were sacrificed, tumor tissues were taken and the tumors were weighed, and major organs and tissues of the mice such as liver, spleen, heart, lung, large intestine, small intestine, and the like were examined.

(3) Experimental Results
Experimental results are shown in Table 3 and Table 4.

TABLE 3

Effects of 14-D-Valine-TPL (DV) on the growth of human acute myelogenous leukemia KG-1a cells in mice in vivo

| | KG-1a | | | | | |
|---|---|---|---|---|---|---|
| | Tumor weight (g) | | | Body weight (g) | | |
| Mouse No. | Control group | DV 0.2 | DV 0.4 | Control group | DV 0.2 | DV 0.4 |
| 1 | 4.06 | 0.5 | 0 | 23.0 (15.11) | 20.4 | 19.1 |
| 2 | 4.14 | 0.42 | 0 | 22.3 (15.38) | 18.5 | 20.4 |
| 3 | 3.06 | 1.49 | 0 | 23.0 (15.97) | 20.2 | 21.0 |
| 4 | | 0.06 | 0 | | 19.9 | 21.1 |
| 5 | | 0.98 | 0 | | 18.1 | 21.4 |
| 6 | | 0.2 | 0 | | 19.0 | 20.8 |

TABLE 4

Effects of 14-D-Valine-TPL (DV) on the growth of human acute myelogenous leukemia THP-1 cells in mice in vivo

| | THP-1 | | | | | |
|---|---|---|---|---|---|---|
| | Tumor weight (g) | | | Body weight (g) | | |
| Mouse No. | Control group | DV 0.2 | DV 0.4 | Control group | DV 0.2 | DV 0.4 |
| 1 | 3.83 | 0.28 | 0 | 23.0 (19.17) | 20.4 | 19.1 |
| 2 | 2.78 | 0 | 0 | 22.3 (19.52) | 18.5 | 20.4 |
| 3 | 3.97 | 0 | 0 | 23.0 (19.03) | 20.2 | 21.0 |
| | | 0.21 | 0 | | 19.9 | 21.1 |
| | | 0.06 | 0 | | 18.1 | 21.4 |
| | | 0 | 0 | | 19.0 | 20.8 |

Note:
DV 0.2: 0.2 mg/kg; DV 0.4: 0.4 mg/kg.

Table 3 and Table 4 show that 14-D-Valine-TPL of the invention can significantly inhibit the growth of two different types of human acute myelogenous leukemia cell lines KG-1a and THP-1 in mice in vivo, and exhibits a significant dose-dependent effect. 14-D-Valine-TPL with a dose of 0.4 mg per kilogram of the body weight enables a complete regression of KG-1a and THP-1 xenograft tumors, with no significant weight losses in the mice. Further, no significant abnormalities were seen in major organs such as heart, lung, liver, spleen, large intestine, small intestine and the like in anatomical examination of the mice. These results indicate that 14-D-Valine-TPL of the invention has a significant activity against different types of human acute myelogenous leukemia, and shows no significant toxic reaction.

EXAMPLE 10

Determination of in vivo Activity of
14-L-Valine-L-Valine-TPL (14-LLV-TPL) Against
Human Leukemia in Mice (1) Experimental Materials
Experiment animal: NOD/SCID mice obtained from the Shanghai Animal Center of the Chinese Academy of Sciences (CAS).
Leukemia cell strain: human KG-1a (acute myelogenous leukemia, AML-M0), obtained from ATCC Library.
Reagent: 14-LLV-TPL trifluoroacetate of the invention, dissolved with sterile PBS to a concentration of 10 mg/ml, and then diluted with sterile deionized water to a required working concentration.
Primary instruments: cell incubator and microplate reader.
(2) Experimental Method
7-week old female NOD/SCID mice were taken and inoculated subcutaneously with $1 \times 10^7$ cells (0.2 ml) per mouse in axilla, with human acute myelogenous leukemia KG-1a cells on the left. When tumors grew to a tumor size of around 50-100 mm$^3$, the mice were randomized into groups with 3 mice each. An equivalent amount of PBS was used for the control group, and the TPL-LLV group was divided into two groups with 0.23 mg/kg body weight and 0.46 mg/kg body weight: intragastric administration, 2 times a day (one at 8 a.m. and one at 4 p.m.) for consecutive 14 days of treatment. An observation was made for total 30 days, during which the conditions of the mice such as tumor size, weight, activity, diet, and the like were measured. At the end of the experiment, the mice were sacrificed, tumor tissues were taken and the tumors were weighed, and major organs and tissues of the mice such as liver, spleen, heart, lung, large intestine, small intestine, and the like were examined.
(3) Experimental Results
Experimental results are shown in Table 5. Table 5 shows that 14-LLV-TPL of the invention can significantly inhibit the growth of human acute myelogenous leukemia cell line KG-1a in mice in vivo, and exhibits a significant dose-dependent effect.

TABLE 5

Effects of 14-LLV-TPL on the growth of human acute myelogenous leukemia KG-1a cells in mice in vivo

| | THP-1 | | | | | |
|---|---|---|---|---|---|---|
| | Tumor volume (mm$^3$) | | | Body weight (g) | | |
| Mouse No. | Control group | LLV 0.23 | LLV0.46 | Control group | LLV 0.23 | LLV0.46 |
| 1 | 1251.54 | 1105.64 | 317.61 | 19.8 | 20.5 | 18.6 |
| 2 | 1196.78 | 804.56 | 383.11 | 18.8 | 19.4 | 20.0 |
| 3 | 2628.39 | 644.07 | 356.82 | 19.1 | 19.7 | 18.9 |
| Overall | 1692.24 ± 811.2 | 851.42 ± 243.33 | 352.51 ± 32.96 | 19.2 ± 0.51 | 19.9 ± 0.57 | 19.2 ± 0.74 |

EXAMPLE 11

Determination of in vivo Activity of 14-L-Valine-D-Valine-TPL (14-DLV-TPL) Against Human Leukemia in Mice (1) Experimental Materials Experiment animal: NOD/SCID mice obtained from the Shanghai Animal Center of the Chinese Academy of Sciences (CAS).
Leukemia cell strain: human KG-1a (acute myelogenous leukemia, AML-M0), obtained from ATCC Library.
Reagent: 14-DLV-TPL trifluoroacetate of the invention, dissolved with sterile PBS to a concentration of 10 mg/ml, and then diluted with sterile deionized water to a required working concentration.
Primary instruments: cell incubator and microplate reader.

(2) Experimental Method 7-week old female NOD/SCID mice were taken and inoculated subcutaneously with $1\times10^7$ cells (0.2 ml) per mouse in axilla, with human acute myelogenous leukemia KG-1a cells on the left. When tumors grew to a tumor size of around 50-100 $mm^3$, the mice were randomized into groups with 3 mice each. An equivalent amount of PBS was used for the control group, and the TPL-DLV group was divided into two groups with 0.23 mg/kg body weight and 0.46 mg/kg body weight: intragastric administration, 2 times a day (one at 8 a.m. and one at 4 p.m.) for consecutive 14 days of treatment. An observation was made for total 30 days, during which the conditions of the mice such as tumor size, weight, activity, diet, and the like were measured. At the end of the experiment, the mice were sacrificed, tumor tissues were taken and the tumors were weighed, and major organs and tissues of the mice such as liver, spleen, heart, lung, large intestine, small intestine, and the like were examined.

(3) Experimental Results

Experimental results are shown in Table 6. Table 6 shows that 14-DLV-TPL of the invention can significantly inhibit the growth of human acute myelogenous leukemia cell line KG-1a in mice in vivo, and exhibits a significant dose-dependent effect.

TABLE 6

Effects of 14-DLV-TPL on the growth of human acute myelogenous leukemia KG-1a cells in mice in vivo

| | THP-1 | | | | | |
|---|---|---|---|---|---|---|
| | Tumor volume ($mm^3$) | | | Body weight (g) | | |
| Mouse No. | Control group | DLV 0.23 | DLV 0.46 | Control group | DLV 0.23 | DLV 0.46 |
| 1 | 1251.54 | 1038.41 | 50.35 | 19.8 | 19.6 | 18.8 |
| 2 | 1196.78 | 562.66 | 90.96 | 18.8 | 19.5 | 19.6 |
| 3 | 2628.39 | 505.81 | 265.32 | 19.1 | 17.8 | 18.5 |
| Overall | 1692.24 ± 811.2 | 702.29 ± 192.47 | 135.54 ± 114.21 | 19.2 ± 0.51 | 19.0 ± 1.01 | 19.0 ± 0.57 |

EXAMPLE 12

Determination of in vivo Activity of 14-L-Phenylalanyl-L-Tyrosine-TPL (14-LPT-TPL) Against Human Leukemia in Mice (1) Experimental Materials Experiment animal: NOD/SCID mice obtained from the Shanghai Animal Center of the Chinese Academy of Sciences (CAS).
Leukemia cell strain: human KG-1a (acute myelogenous leukemia, AML-M0), obtained from ATCC Library.
Reagent: 14-LPT-TPL trifluoroacetate of the invention, dissolved with sterile PBS to a concentration of 10 mg/ml, and then diluted with sterile deionized water to a required working concentration.
Primary instruments: cell incubator and microplate reader.

(2) Experimental Method 7-week old female NOD/SCID mice were taken and inoculated subcutaneously with $1\times10^7$ cells (0.2 ml) per mouse in axilla, with human acute myelogenous leukemia KG-1a cells on the left. When tumors grew to a tumor size of around 50-100 $mm^3$, the mice were randomized into groups with 3 mice each. An equivalent amount of PBS was used for the control group, and the TPL-DLV group was divided into two groups with 0.32 mg/kg body weight and 0.64 mg/kg body weight: intragastric administration, 2 times a day (one at 8 a.m. and one at 4 p.m.) for consecutive 14 days of treatment. An observation was made for total 30 days, during which the conditions of the mice such as tumor size, weight, activity, diet, and the like were measured. At the end of the experiment, the mice were sacrificed, tumor tissues were taken and the tumors were weighed, and major organs and tissues of the mice such as liver, spleen, heart, lung, large intestine, small intestine, and the like were examined.

(3) Experimental Results

Experimental results are shown in Table 7. Table 7 shows that 14-LPT-TPL of the invention can significantly inhibit the growth of human acute myelogenous leukemia cell line KG-1a in mice in vivo, and exhibits a significant dose-dependent effect.

TABLE 7

Effects of 14-LPT-TPL on the growth of human acute myelogenous leukemia KG-1a cells in mice in vivo

| | THP-1 | | | | | |
|---|---|---|---|---|---|---|
| | Tumor volume ($mm^3$) | | | Body weight (g) | | |
| Mouse No. | Control group | LPT 0.32 | LPT 0.64 | Control group | LPT 0.32 | LPT 0.64 |
| 1 | 1251.54 | 131.17 | 0 | 19.8 | 21.4 | 17.4 |
| 2 | 1196.78 | 168.07 | 0 | 18.8 | 20 | 19.4 |
| 3 | 2628.39 | 93.12 | 0 | 19.1 | 20.4 | 16.1 |
| Overall | 1692.24 ± 811.2 | 130.78 ± 37.48 | 0 | 19.2 ± 0.72 | 20.6 ± 1.01 | 17.6 ± 1.66 |

EXAMPLE 13

Determination of in vivo Activity of 14-D-Valine-D-Valine-TPL (14-DDV-TPL) Against Human Leukemia in Mice (1) Experimental Materials Experiment animal: NOD/SCID mice obtained from the Shanghai Animal Center of the Chinese Academy of Sciences (CAS). Leukemia cell strain: human K562/ADR (chronic myelogenous leukemia, CML), obtained from ATCC Library. Reagent: 14-DDV-TPL trifluoroacetate of the invention, dissolved with sterile PBS to a concentration of 10 mg/ml, and then diluted with sterile deionized water to a required working concentration. Primary instruments: cell incubator and microplate reader.

(2) Experimental Method 7-week old female NOD/SCID mice were taken and inoculated subcutaneously with $1\times10^7$ cells (0.2 ml) per mouse in axilla, with human K562/ADR cells on the left. When tumors grew to a tumor size of around 50-100 mm³, the mice were randomized into groups with 3 mice each. An equivalent amount of PBS was used for the control group, and the TPL-DDV group was divided into two groups with 0.23 mg/kg body weight and 0.46 mg/kg body weight: intragastric administration, 2 times a day (one at 8 a.m. and one at 4 p.m.) for consecutive 14 days of treatment. An observation was made for total 30 days, during which the conditions of the mice such as tumor size, weight, activity, diet, and the like were measured. At the end of the experiment, the mice were sacrificed, tumor tissues were taken and the tumors were weighed, and major organs and tissues of the mice such as liver, spleen, heart, lung, large intestine, small intestine, and the like were examined.

(3) Experimental Results

Experimental results are shown in Table 8. Table 8 shows that 14-DDV-TPL of the invention can significantly inhibit the growth of human chronic myelogenous leukemia cell line K562/ADR cells in mice in vivo, and exhibits a significant dose-dependent effect.

TABLE 8

Effects of 14-DDV-TPL on the growth of human chronic myelogenous leukemia K562/ADR cells in mice in vivo

| | K562/ADR | | | | | |
|---|---|---|---|---|---|---|
| | Tumor volume (mm³) | | | Body weight (g) | | |
| Mouse No. | Control group | DDV 0.23 | DDV 0.46 | Control group | DDV 0.23 | DDV 0.46 |
| 1 | 209.97 | 0 | 0 | 21 | 19.1 | 19.3 |
| 2 | 1059.16 | 0 | 0 | 20.3 | 19.7 | 20.5 |
| 3 | 0 | 0 | 0 | 16.3 | 21.2 | 23.2 |
| Overall | 423.04 ± 560.81 | 0 | 0 | 19.2 ± 2.54 | 20.0 ± 1.08 | 21.0 ± 2.0 |

EXAMPLE 14

Determination of in vivo Activity of 14-L-Valine-TPL (14-LV-TPL) Against Human Leukemia in Mice (1) Experimental Materials Experiment animal: NOD/SCID mice obtained from the Shanghai Animal Center of the Chinese Academy of Sciences (CAS).

Leukemia cell strain: human K562/ADR (chronic myelogenous leukemia, CML), obtained from ATCC Library.

Reagent: 14-LV-TPL trifluoroacetate of the invention, dissolved with sterile PBS to a concentration of 10 mg/ml, and then diluted with sterile deionized water to a required working concentration.

Primary instruments: cell incubator and microplate reader.

(2) Experimental Method 7-week old female NOD/SCID mice were taken and inoculated subcutaneously with $1\times10^7$ cells (0.2 ml) per mouse in axilla, with human K562/ADR cells on the left. When tumors grew to a tumor size of around 50-100 mm³, the mice were randomized into groups with 3 mice each. An equivalent amount of PBS was used for the control group, and the TPL-LV group was divided into two groups with 0.2 mg/kg body weight and 0.4 mg/kg body weight: intragastric administration, 2 times a day (one at 8 a.m. and one at 4 p.m.) for consecutive 14 days of treatment. An observation was made for total 30 days, during which the conditions of the mice such as tumor size, weight, activity, diet, and the like were measured. At the end of the experiment, the mice were sacrificed, tumor tissues were taken and the tumors were weighed, and major organs and tissues of the mice such as liver, spleen, heart, lung, large intestine, small intestine, and the like were examined.

(3) Experimental Results

Experimental results are shown in Table 9. Table 9 shows that 14-LV-TPL of the invention can significantly inhibit the growth of human chronic myelogenous leukemia cell line K562/ADR cells in mice in vivo, and exhibits a significant dose-dependent effect.

TABLE 9

Effects of 14-LV-TPL on the growth of human chronic myelogenous leukemia K562/ADR cells in mice in vivo

| | K562/ADR | | | | | |
|---|---|---|---|---|---|---|
| | Tumor volume (mm³) | | | Body weight (g) | | |
| Mouse No. | Control group | LV 0.2 | LV 0.4 | Control group | LV 0.2 | LV 0.4 |
| 1 | 209.97 | 159.87 | 0 | 21 | 22 | 21.1 |
| 2 | 1059.16 | 73.63 | 30.71 | 20.3 | 18 | 21.2 |
| 3 | 0 | 0 | 96.79 | 16.3 | 22.2 | 20.8 |
| | 423.04 ± 560.81 | 77.83 ± 80.02 | 42.50 ± 49.46 | 19.2 ± 2.54 | 20.7 ± 2.37 | 21.0 ± 0.21 |

EXAMPLE 15

Determination of the Activity of 14-D-Valine-TPL for Inhibiting T Lymphocytes and B Lymphocytes in vitro (1) Experimental Materials Leukemia cell strains: Jurkat (T lymphocyte), H9 (T lymphocyte), CEM (B lymphocyte), and Sup-B15 (B lymphocyte).

Primary reagent: 14-D-Valine-TPL of the invention.

Primary instruments: cell incubator and microplate reader.

(2) Experimental Method 5000 well-grown lymphocytes were taken and seeded into wells of a 96-well cell culture plate. The medium was 1640 cell medium containing 10% fetal bovine serum. 14-D-Valine-TPL with different concentrations was added, and after being uniformly mixed, the plate was placed in a carbon dioxide (5% $CO_2$) cell incubator, and incubated at 37° C. for 72 hours. The concentration of live cells was then determined using the MTT assay. In this experiment, the cell viability in the control group (without the compound treatment) was set to be 100%, and the cell viability (%) after the action of the compound and the half maximal growth inhibitory concentration of leukemia cells at 72 hours ($IC_{50}$ value at 72 hours) were calculated.

(3) Experimental Results

Experimental results are shown in Table 10. Table 10 shows that 14-D-Valine-TPL of the invention can significantly inhibit the growth of these T lymphocytes and B lymphocytes.

TABLE 10

Inhibitory effects of 14-D-Valine-TPL on T/B lymphocytes proliferation

| Immune Cell Line | 14-D-Valine-TPL IC50 (nM/L) |
| --- | --- |
| Jurkat (T lymphocyte) | 36.301 |
| CEM (B lymphocyte) | 25.488 |
| Molt-4 (T lymphocyte) | 10.824 |
| Sup-B15 (B lymphocyte) | 20.674 |

EXAMPLE 16

Expression of Transcription Factor TFIIH Subunit XPB and RNA Polymerase II (Pol II) in Different Types of Tumor Cells and Normal Cells It has been reported in some literatures that transcription factor TFIIH subunit XPB (xeroderma pigmentosum group B) and RNA polymerase II (Pol II) are the key target molecules for triptolide to exert its pharmacological effect [Titov D V, et al., "XPB, a subunit of TFIIH, is a target of the natural product triptolide." Nature chemical biology. 2011, 7:182-188]. In order to know whether the expression levels of XPB and Pol II in tumor cells and normal cells are different, the present invention adopts the immunoblot technique to detect the protein levels of XPB and Pol II in different types of tumor cells and normal cells.

(1) Experimental Materials

Leukemia cell strains: Nalm6 (lymphoma), Jurkat (acute lymphoblastic leukemia), THP-1 (acute monocytic leukemia), KG-1a (acute myelogenous leukemia), HL-60 (acute myelogenous leukemia), NB4 (acute promyelocytic leukemia), and U937 (acute monocytic leukemia). Normal blood cell samples were obtained from volunteers.

(2) Experimental Method: the Conventional Immunoblot Technique.

Cellular proteins of leukemia cell and normal cell samples were extracted according to conventional methods, and separated through SDS-PAGE protein electrophoresis, and then transferred to NC membrane. Experimental procedures such as incubation with primary antibody and secondary antibody, development, exposure, and the like were performed according to conventional methods. GAPDH served as an internal reference protein. Results: As shown in FIG. 1, XPB and Pol II proteins were highly expressed in most tumor cells, and were expressed at low levels or not expressed in normal blood cells. This result indicates that the diseases related to abnormally high expression of XPB and Pol II may serve as the indications of triptolide and derivatives thereof.

FIG. 1 shows the results of the expression levels of XPB and Pol II in different types of tumor cells and normal cells detected by adopting the immunoblot technique. 1: normal blood cells; 2: Nalm6; 3: Jurkat; 4: THP-1; 5: KG-1a; 6: HL-60; 7: NB4; 8: U937.

EXAMPLE 17

Inhibitory Effects of 14-D-Valine-TPL on the Activities of XPB and Pol II in Human THP-1 Leukemia Cells XPB and Pol II are known to be the key target molecules for triptolide to exert its pharmacological effect [Titov D V, et al., "XPB, a subunit of TFIIH, is a target of the natural product triptolide." Nature chemical biology. 2011, 7:182-188]. In order to know whether the compounds of the invention have the activity to inhibit these two target molecules, the present invention adopts the cell culture technique and immunoblot technique to detect the effect of 14-D-Valine-TPL on the activities of XPB and Pol II in leukemia cells.

(1) Experimental Materials

Leukemia cell strain: human THP-1 leukemia cell strain (acute myelogenous leukemia-M5, AML-M5).

Reagent: 14-D-Valine-TPL.

(2) Experimental Method

Well-grown leukemia cells were taken and seeded into wells of a 6-well cell culture plate, with a density of $1\times10^6$/ml. The medium was 1640 cell medium containing 10% fetal bovine serum. 14-D-Valine-TPL with different concentrations was added, and after being uniformly mixed, the plate was placed in a carbon dioxide (5% $CO_2$) cell incubator, and incubated at 37° C. for 48 hours. Cellular proteins were then extracted, and the immunoblot technique was used to detect the expression levels of XPB and Pol II.

(3) Experimental Results

Figure 2:
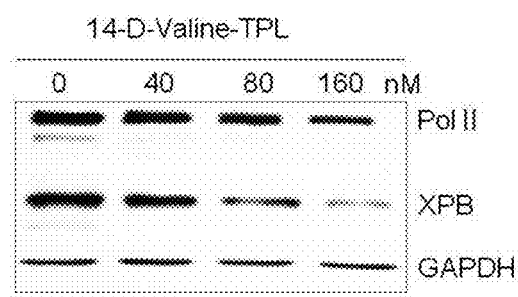
FIG. 2 shows the results of the immunoblot analysis of the inhibitory effects of 14-D-Valine-TPL on the activities of XPB and Pol II in human THP-1 leukemia cells.

Experimental results are shown in FIG. 2. 14-D-Valine-TPL down-regulated the levels of XPB and Pol II in a dose-dependent manner. It can be seen that 14-D-Valine-TPL significantly inhibited the levels of XPB and Pol II in THP-1 cells at a concentration of 160 nM. These results indicate that the 14-D-Valine-TPL compound of the invention can inhibit the activities of XPB and Pol II, and is useful for the diseases related to abnormally high expressions of XPB and Pol II.

FIG. 2 is the results of the inhibitory effects of 14-D-Valine-TPL on the activities of XPB and Pol II in human THP-1 leukemia cells detected by adopting the cell culture technique and the immunoblot technique.

EXAMPLE 18

Inhibitory Effects of 14-D-Valine-TPL on the Activity of c-Myc Oncogene in Human K562 Leukemia Cells Oncogene c-myc is known to also be one of the key target molecules for triptolide to exert its pharmacological effect [Stéphan Vispé, et al., "Triptolide is an inhibitor of RNA polymerase I and II-dependent transcription leading predominantly to down-regulation of short-lived mRNA." Mol Cancer Ther 2009; 8:2780-2790]. In order to know whether the compounds of the invention have the activity to inhibit c-myc, the present invention adopts the cell culture technique and immunoblot technique to detect the effect of 14-D-Valine-TPL on the activity of c-myc in leukemia cells.

(1) Experimental Materials

Leukemia cell strain: human K562 leukemia cell strain (acute transformation of chronic myelogenous leukemia).

Reagent: 14-D-Valine-TPL.

(2) Experimental Method

Well-grown leukemia cells were taken and seeded into wells of a 6-well cell culture plate, with a density of $1\times10^6$/ml. The medium was 1640 cell medium containing 10% fetal bovine serum. 14-D-Valine-TPL with different concentrations was added, and after being uniformly mixed, the plate was placed in a carbon dioxide (5% $CO_2$) cell incubator, and incubated at 37° C. for 48 hours. Cellular proteins were then extracted, and the immunoblot technique was used to detect the expression level of c-myc.

(3) Experimental Results

Figure 3:
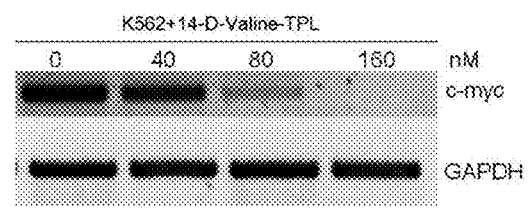
FIG. 3 shows the results of the immunoblot analysis of the inhibitory effects of 14-D-Valine-TPL on the activity of c-myc in human K562 leukemia cells.

Experimental results are shown in FIG. 3. 14-D-Valine-TPL down-regulated the level of c-myc protein in a dose-dependent manner. It can be seen that 14-D-Valine-TPL significantly inhibited the level of c-myc in K562 cells at a concentration of 80 nM. This result indicates that the 14-D-Valine-TPL compound of the invention can inhibit the activity of oncogene c-myc in tumor cells, and is useful for the diseases related to abnormally high expression of c-myc.

What is claimed is:

1. A C14-hydroxyl esterified amino acid derivative of triptolide selected from the following compounds:

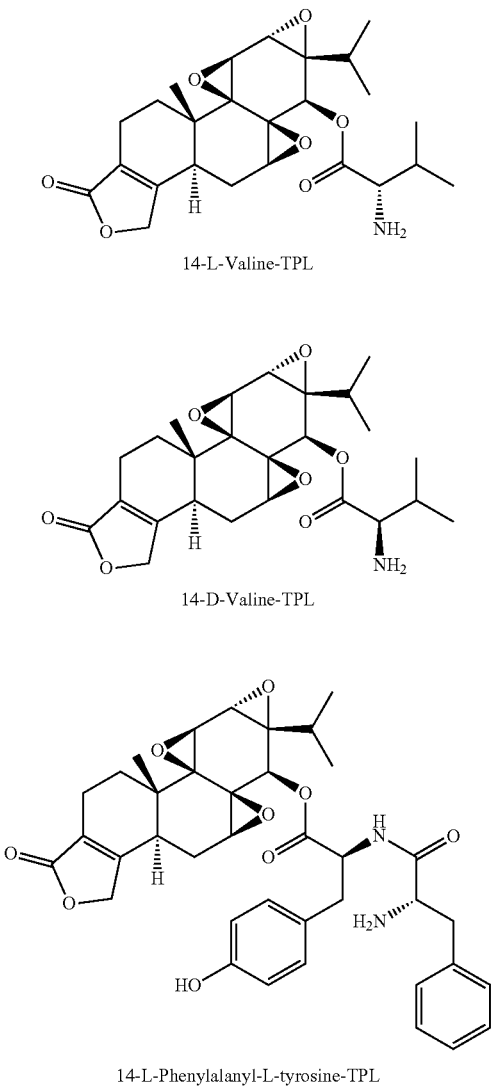

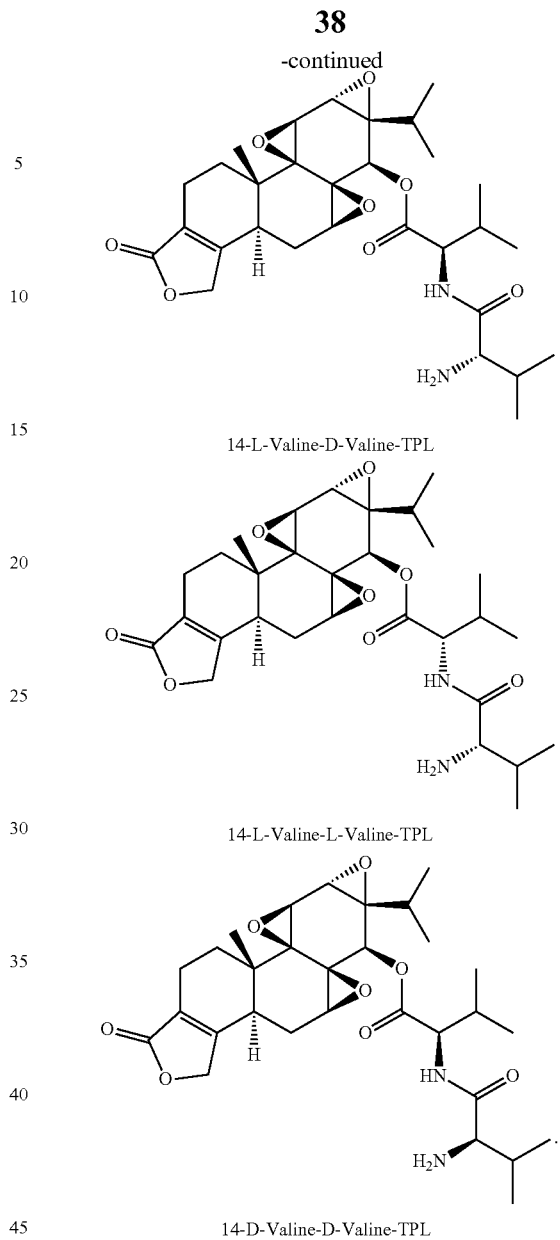

2. A pharmaceutical composition, comprising the C14-hydroxyl esterified amino acid derivative of triptolide according to claim 1, and an optional pharmaceutically acceptable excipient.

3. A pharmaceutically acceptable salt of the C14-hydroxyl esterified amino acid derivative of triptolide according to claim 1.

* * * * *

UNITED STATES PATENT AND TRADEMARK OFFICE
CERTIFICATE OF CORRECTION

PATENT NO. : 10,238,623 B2
APPLICATION NO. : 15/551695
DATED : March 26, 2019
INVENTOR(S) : Xu Page 1 of 1

It is certified that error appears in the above-identified patent and that said Letters Patent is hereby corrected as shown below:

On the Title Page

Under Item (12), delete "Xu et al." and insert --Xu--

Item (72), Line 2, delete "Hongjian Jiang, Hangzhou (CN)"

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*